(12) United States Patent
Habboushe

(10) Patent No.: US 11,382,873 B1
(45) Date of Patent: Jul. 12, 2022

(54) ORAL ADMINISTRATION OF KETAMINE

(71) Applicant: Vitalis Analgesics LLC, Wilmington, DE (US)

(72) Inventor: Joseph Habboushe, New York, NY (US)

(73) Assignee: Vitalis Analgesics LLC, Wilmington, DE (US)

( * ) Notice: Subject to any disclaimer, the term of this patent is extended or adjusted under 35 U.S.C. 154(b) by 0 days.

(21) Appl. No.: 17/412,110

(22) Filed: Aug. 25, 2021

Related U.S. Application Data

(60) Provisional application No. 63/135,126, filed on Jan. 8, 2021, provisional application No. 63/176,654, filed on Apr. 19, 2021, provisional application No. 63/235,413, filed on Aug. 20, 2021.

(51) Int. Cl.

| | |
|---|---|
| *A61K 9/20* | (2006.01) |
| *A61K 31/135* | (2006.01) |
| *A61K 9/00* | (2006.01) |
| *A61P 25/04* | (2006.01) |
| *A61K 31/616* | (2006.01) |

(52) U.S. Cl.
CPC .......... *A61K 31/135* (2013.01); *A61K 9/0053* (2013.01); *A61K 9/0056* (2013.01); *A61K 31/616* (2013.01); *A61P 25/04* (2018.01)

(58) Field of Classification Search
None
See application file for complete search history.

(56) References Cited

U.S. PATENT DOCUMENTS 5,840,731 A * 11/1998 Mayer ................ A61P 25/04
514/289
2015/0072005 A1 * 3/2015 Habboushe .......... A61K 31/522
424/471

* cited by examiner

*Primary Examiner* — Susan T Tran
(74) *Attorney, Agent, or Firm* — Sheppard Mullin Richter & Hampton LLP

(57) ABSTRACT

Disclosed are pharmaceutical compositions having a portion of ketamine for intraoral release and another ketamine for gastrointestinal release. The compositions can further include aspirin. The disclosed formulations and related administration approaches improve the bioavailability and efficacy of oral ketamine.

6 Claims, 10 Drawing Sheets

ORAL ADMINISTRATION OF KETAMINE

CROSS REFERENCE TO RELATED APPLICATIONS

This application claims the benefit under 35 U.S.C. § 119(e) of U.S. Provisional Application Ser. No. 63/135,126, filed Jan. 8, 2021, 63/176,654, filed Apr. 19, 2021, and 63/235,413, filed Aug. 20, 2021, the contents of which are incorporated by reference in their entirety into the present disclosure.

BACKGROUND

Acute Pain is one of the most frequent chief complaints and the main reason for visiting the Emergency Department (ED). The acute pain in the ED is largely prevalent across the country with recent literature demonstrating that 61-91% of patients are admitted to the ED due to a variety of acute painful syndromes. Musculoskeletal pain (MSK) affects one out of three adults and it is the most common source of serious long term pain and physical disability. Furthermore, studies have demonstrated that the frequency for analgesia for adults who received treatment for musculoskeletal pain in the ED is between 11-29%.

To complicate the issue of MSK pain management even further, the opioid epidemic spanning over 20 years in the USA and claiming over 400,000 deaths from unintentional prescription opioid overdose, has forced health care systems and hospitals across the nation to reduce the reliance on opioid analgesics and embrace the utility of non-opioid analgesia. Several classes of non-opioid analgesics such as acetaminophen, NSAID's (aspirin, ibuprofen, diclofenac) and ketamine have gained great deal of attention as viable alternatives to opioids in management of acute MSK pain in the ED.

Ketamine is commonly used for anesthesia. It induces a trance-like state while providing pain relief, sedation, and memory loss. Other uses include sedation in intensive care and treatment of pain and depression. Heart function, breathing, and airway reflexes generally remain functional. Common side effects include agitation, confusion, or hallucinations as the medication wears off. Elevated blood pressure and muscle tremors are also common. Spasms of the larynx may occur, but relatively infrequently.

Ketamine was discovered in 1962, first tested in humans in 1964, and approved for use in the United States in 1970. It is on the World Health Organization's List of Essential Medicines. It is also used as a recreational drug for its hallucinogenic and dissociative effects.

Ketamine can be absorbed by intravenous, intramuscular, oral, and topical routes due to both its water and lipid solubilities. In medical settings, ketamine is usually injected intravenously or intramuscularly. Oral ketamine, however, is easily broken down by bile acids, and hence has a low bioavailability. Bioavailability through the oral route reaches 17 to 29%. By contrast, bioavailability through intramuscular injection is about 93%.

The onset of action of ketamine is seconds intravenously and 1 to 5 minutes intramuscularly, but 15 to 30 minutes orally. Moreover, maximal concentrations of ketamine are reached in 1 to 3 minutes intravenously, and 5 to 15 minutes intramuscularly, but 30 minutes orally.

There is a need to develop oral formulations for ketamine with improved bioavailability and faster action.

SUMMARY

It has been discovered that oral administration of ketamine achieved a remarkably higher bioavailability when the ketamine was partially released intraorally and delivered transmucosally and partially released through the gastrointestinal (GI) track, as compared to intraoral or GI release alone. Further, certain desired effects of ketamine, such as pain (acute pain, acute on chronic pain, chronic pain) reduction, suppression of depression, reduction of fatigue (e.g., multiple sclerosis fatigue), reduction of suicidality, treatment of asthma/reactive airway, treatment of cannabinoid hyperemesis syndrome exacerbations, and treatment of Alzheimer's/dementia can be further enhanced by co-administration with aspirin which meanwhile can reduce the undesired effects of ketamine, including its sedation effect and addiction potential.

In accordance with one embodiment of the present disclosure, therefore, provided is a pharmaceutical composition comprising a first portion comprising a first amount of ketamine, and a second portion comprising a second amount of ketamine, wherein, upon oral administration to a subject, the first portion disintegrates or dissolves intraorally substantively providing rapid release of the ketamine of the first portion, and the second portion is substantially more difficult than the first portion to disintegrate or dissolve intraorally but is ingestible and releasable in the gastrointestinal track of the subject.

The pharmaceutical composition can be in the form of a tablet or capsule. In one aspect, the second portion is enclosed within the first portion. In one aspect, the first portion is chewable. In another aspect, the first portion is in the form of molded triturate.

In one aspect, the second portion is compressed. In another aspect, the hardness of the second portion is at least about 10 kilopascal (kp). In yet another aspect, the second portion further comprises a pharmaceutically acceptable flavoring agent not present in the first portion.

In any of the above embodiments, the pharmaceutical composition further comprises a third portion that comprises an effective amount of aspirin. In still another aspect, the aspirin is part of the first portion or the second portion. In one aspect, the aspirin is present in both the first portion and the second portion.

Another embodiment of the present disclosure provides a method of administering ketamine to a subject, comprising administering to the subject (a) a first composition comprising a first amount of ketamine and (b) a second composition comprising a second amount of ketamine, wherein the first composition disintegrates or dissolves intraorally substantively providing rapid release of the ketamine of the first portion, and the second composition is ingested and released in the gastrointestinal track of the subject.

In one aspect of such a method, the administration is within 30 minutes following a meal. In another aspect, the administration is accompanied by oral administration of an acidic drink which can assist transmucosal absorption of the first ketamine composition.

Also provided is a method of administering ketamine to a subject with improved bioavailability, comprising administering to the subject a first composition comprising a first amount of ketamine and a second composition comprising a second amount of ketamine, wherein the first composition disintegrates or dissolves intraorally within 10 minutes permitting rapid release of the ketamine in the first composition, and the second composition is ingested and released in the gastrointestinal track of the subject.

Either of these methods can further comprise administering to the subject an effective amount of aspirin, along with the first composition or the second composition, or both.

Another embodiment provides a pharmaceutical composition comprising ketamine and aspirin. In some embodiments, the composition comprises a first portion comprising a first amount of the aspirin, and a second portion comprising a second amount of the aspirin, wherein, upon oral administration to a subject, the first portion disintegrates or dissolves intraorally providing rapid release of the aspirin of the first portion, and the second portion is substantially more difficult than the first portion to disintegrate or dissolve intraorally but is ingestible and releasable in the gastrointestinal track of the subject.

Also provided is a method of administering ketamine to a subject, comprising administering to the subject ketamine and aspirin. In some embodiments, the aspirin is administered as (a) a first composition comprising a first amount of aspirin and (b) a second composition comprising a second amount of aspirin, wherein the first composition disintegrates or dissolves intraorally providing rapid release of the aspirin of the first portion, and the second composition is ingested and released in the gastrointestinal track of the subject.

In another embodiment, provided is a pharmaceutical composition comprising ketamine and a glutamate ionotropic receptor NMDA type subunit 2A (GRIN2A) modulator. Examples include aspirin, nicotine, propofol, melatonin and GQ1b.

Also provided is a method of administering ketamine to a subject, comprising administering to the subject ketamine and a GRIN2A modulator.

Still further provided is a GRIN2A modulator for use in enhancing the efficacy of pain relief, or reducing the side effects of ketamine.

DETAILED DESCRIPTION

Figure 1:
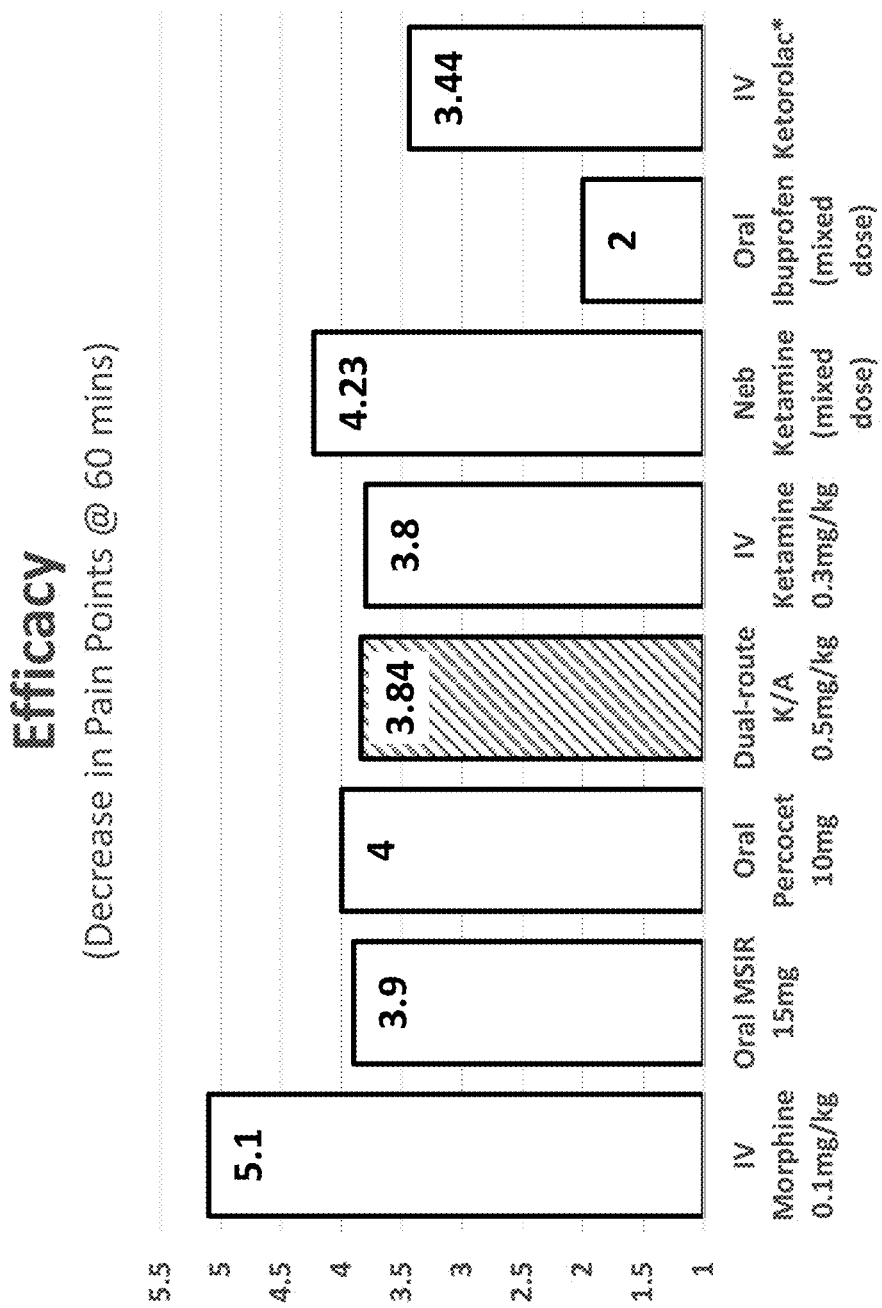
FIG. 1 compares the pain reduction efficacies of different treatments.

The present disclosure provides pharmaceutical compositions for oral administration of ketamine.

A. Definitions

Unless defined otherwise, the terms used herein are intended to have their ordinary meaning in the art.

All numerical designations, e.g., pH, temperature, time, concentration, and weight, including ranges, are approximations that typically may be varied (+) or (−) by increments of 0.1, 1.0, 10.0, or 100.0 as appropriate. It is to be understood, although not always explicitly stated, that all numerical designations are preceded by the term "about".

"About" will be understood by persons of ordinary skill in the art and will vary to some extent on the context in which the term is used. If there are uses of the term which are not clear to persons of ordinary skill in the art given the context in which it is used, "about" will mean up to plus or minus 10%, or 5%, or 2% or 1% or 0.5% of the particular term.

As used herein, the term "comprising" means any recited elements are necessarily included and other elements may optionally be included. "Consisting essentially of" means any recited elements are necessarily included, elements that would materially affect the basic and novel characteristics of the listed elements are excluded, and other elements may optionally be included. "Consisting of" means that all elements other than those listed are excluded. Embodiments defined by each of these terms are within the scope of this invention.

As used in the specification and claims, the singular form "a", "an", and "the" includes plural references unless the context clearly dictates otherwise.

"Administering" or "administration of" a drug to a patient (and grammatical equivalents of this phrase) refers to direct administration, which may be administration to a patient by a medical professional or may be self-administration, and/or indirect administration, which may be the act of prescribing a drug. For example, a physician who instructs a patient to self-administer a drug and/or provides a patient with a prescription for a drug is administering the drug to the patient.

As used herein, "compressed" dosage form (e.g., "compressed portion"), refers to a dosage form comprising a compressed powder. For example, a compressed portion may be formed using a rotary tablet press or other similar machinery known to one of skill in the art.

As used here, "disintegrates or dissolves intraorally" refers to that a majority of a composition or a portion of a composition, such as a tablet or a capsule, breaks apart into smaller particles intraorally. The majority, in one aspect, means at least about 50%, or alternatively at about 60%, or 70%, or 80%, or 90%, or 95%, or 98%, or 99%.

As used herein, "bilayer" compressed dosage form (e.g., "bilayer tablet") refers to a single compressed dosage form comprising two layers. A bilayer compressed dosage form can be made in a single compression step. Likewise, a "trilayer" compressed dosage form (e.g., "trilayer tablet") refers to a single compressed dosage form comprising three layers.

As used herein, "wet granulation" refers to a process known in the pharmaceutical arts that involves forming granules by the addition of a liquid, such as purified water, alcohol, or a binder solution.

"Controlled release form" refers to a formulation in which the aspirin is included within a matrix, which matrix can be either insoluble, soluble, or partly soluble. Controlled release matrix formulations of the insoluble type are also referred to as insoluble polymer matrices, swellable matrices, or lipid matrices depending on the components that make up the matrix. Controlled release matrix formulations of the soluble type are also referred to as hydrophilic colloid matrices, erodible matrices, or reservoir systems. Controlled release formulations of the present disclosure refer to formulations comprising an insoluble matrix, a soluble matrix or a combination of insoluble and soluble matrices in which the rate of release is slower than that of an uncoated non-matrix or immediate release formulations or uncoated normal release matrix formulations. Controlled release formulations can be coated with a control releasing coat to further slow the release of aspirin from the controlled release matrix formulation. Such coated controlled release matrix formulations can exhibit modified-release, controlled-release, sustained-release, extended-release, prolonged-release, delayed-release, or combinations thereof, of aspirin. Examples of controlled release forms of aspirin include Slo-Aspirin® available from Upsher Smith Laboratories, Inc. (Maple Grove, Minn.).

"Controlled release coat" refers to a functional coat which can, for example, include at least one pH independent or pH dependent (such as for example enteric or reverse enteric types) polymer, soluble or insoluble polymer, lipids or lipidic materials, or combinations thereof, which, when applied onto a formulation can slow (for example, when applied to an immediate release formulation or a normal release matrix formulation), further slow (for example when applied to a controlled release matrix formulation), or modify the rate of release of aspirin.

"Excipient" refers to a pharmacologically inactive substance used with the active agents or drugs of a medication or a formulation. Excipients are also sometimes used to bulk up formulations that contain very potent active ingredients, to allow for convenient and accurate dosage. In addition to their use in the unit dose forms, excipients can be used in the manufacturing process to aid in the handling of the active substance concerned. Depending on the route of administration, and form of medication, different excipients may be used. Examples of an excipient includes, without limitation, one or more of the following: an additive, an anti-foaming agent, a binder, a chemical stabilizer, a coloring agent, a diluent, a disintegrating agent, an emulsifying agent, a filler, a flavoring agents, a glidant, a lubricant, a pH modifier, a plasticizer, a solubilizer, a swelling enhancer, a spheronization aid, a solubility enhancer, or a suspending agent.

"Immediate release formulation" refers to a formulation from which the drug is released without any substantial delay and substantially at once.

"Patient" or "subject" refers to mammals, including humans and animals, such as simians, cattle, horses, dogs, cats, and rodents having the need to take aspirin.

"Pharmaceutically acceptable salt" refers to pharmaceutically acceptable salts derived from a variety of organic and inorganic counter ions well known in the art that include, by way of example only, sodium, potassium, calcium, magnesium, ammonium, and tetraalkylammonium, and when the molecule contains a basic functionality, salts of organic or inorganic acids, such as hydrochloride, hydrobromide, tartrate, mesylate, acetate, maleate, and oxalate. Suitable salts include those described in P. Heinrich Stahl, Camille G. Wermuth (Eds.), Handbook of Pharmaceutical Salts Properties, Selection, and Use, 2002, incorporated herein by reference.

"Plasticizer" refers to a compound capable of plasticizing or softening a polymer or a binder. Plasticizers can broaden the average molecular weight of a polymer in which they are included thereby lowering its glass transition temperature or softening point. Plasticizers also can reduce the viscosity of a polymer. The use of plasticizers is optional, but they can be included in a formulation to modify the properties and characteristics of the polymers used in the coat(s) or core of the formulation for convenient processing during manufacture of the coat(s) and/or the core of the formulation. Once the coat(s) and/or core has been manufactured, certain plasticizers can function to increase the hydrophilicity of the coat(s) and/or core of the formulation in the environment of use. During manufacture of the coat(s) and/or core, the plasticizer can lower the melting temperature or glass transition temperature (softening point temperature) of the polymer or binder.

"Solid formulation" refers to a formulation that is neither liquid nor gaseous. Solid formulations include tablets, powders, microparticles, capsules, matrix forms, suppositories, sachets, troches, patches and lozenges. Solid formulations in the form of capsules contain a solid composition within a capsule that can be made of gelatin or other encapsulating material. Liquid formulations include liquid suspensions and elixirs.

"Swelling enhancer" refers to an excipient that swells rapidly resulting in an increase in the size of the tablet. At lower concentrations, these excipients can be used as super disintegrants; however at higher concentrations, e.g., at concentrations above about 5% w/w, these excipients function as swelling enhancers and increase the size of the matrix formulation.

"Therapeutically effective amount" refers to an amount of the drug that, when administered to a patient, will have the intended therapeutic effect, e.g., alleviation, amelioration, palliation or elimination of one or more manifestations of cancer or other hyperproliferative disease in the patient. A therapeutic effect does not necessarily occur by administration of one dose, and may occur only after administration of a series of doses. Typically, cancer drugs are administered in a repeating series of doses, and in certain instances each series may be referred to as a "cycle" of therapy. Thus, a therapeutically effective amount may be administered in one or more administrations.

"Treating" or "treatment of" a condition or patient refers to taking steps to obtain beneficial or desired results, including clinical results. For purposes of this disclosure, beneficial or desired clinical results include, but are not limited to, in intended treatment purpose of ketamine such as pain, anesthesia, asthma, depression, or other beneficial results including reduction of side effects.

B. Oral Formulations

Figure 2:
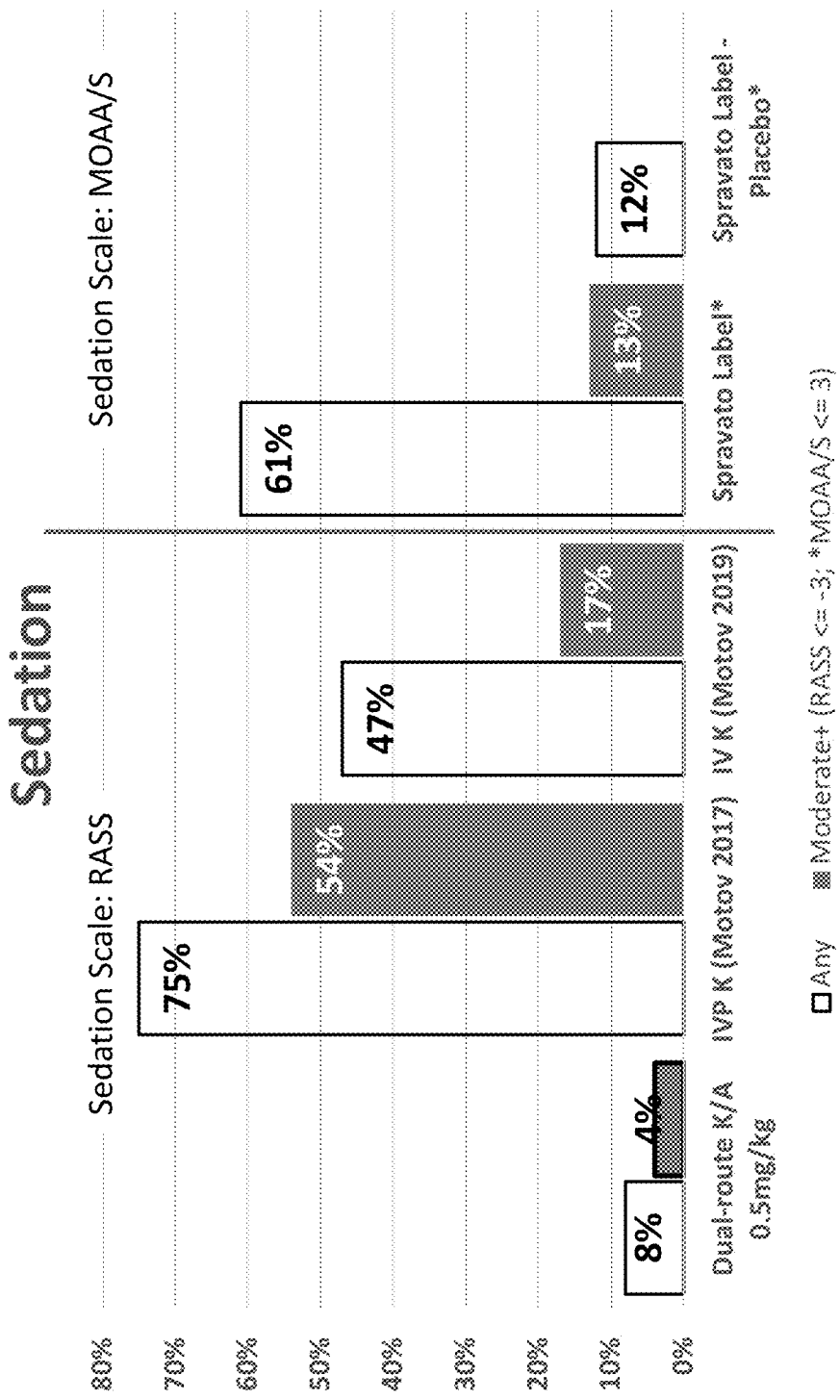
FIG. 2 compares the sedation side effects of different treatments.
Figure 3:
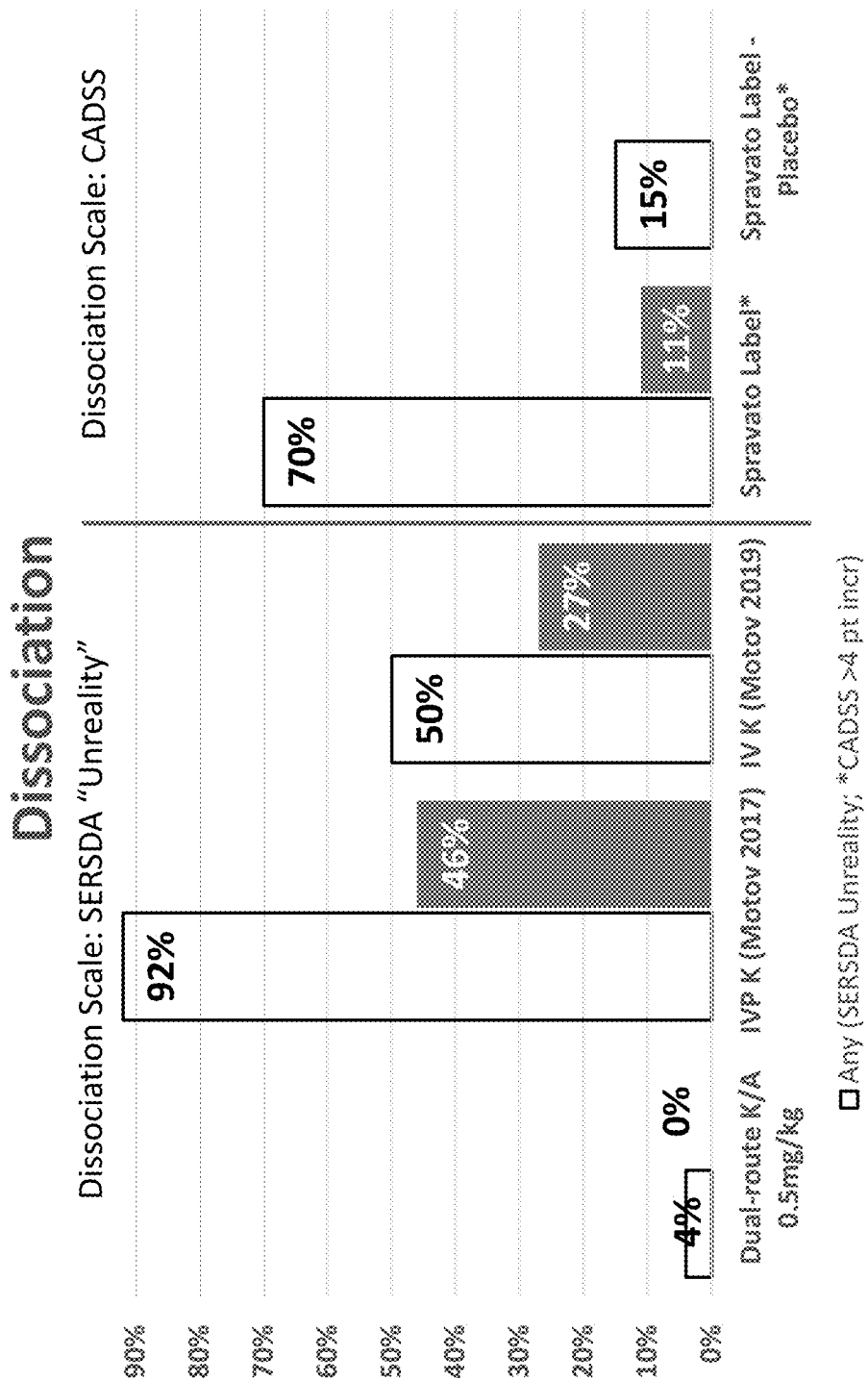
FIG. 3 compares the disassociation side effects of different treatments.

As demonstrated in the accompanying experimental examples, when ketamine was administered with aspirin through two different route of administration (intraoral and oral) its efficacy was even better than intravenously administered ketamine and was close to orally administered MSIR (Morphine) (FIG. 1), and furthermore significantly better than intravenously administered ketamine if corrected for expected bioavailability of oral ketamine (oral ketamine is about 18-20% bioavailable, while IV ketamine is about 100% bioavailable). Meanwhile, the sedation and dissociation side effects were considerably reduced as compared to intravenously administered ketamine (FIG. 2-3).

Figure 4:
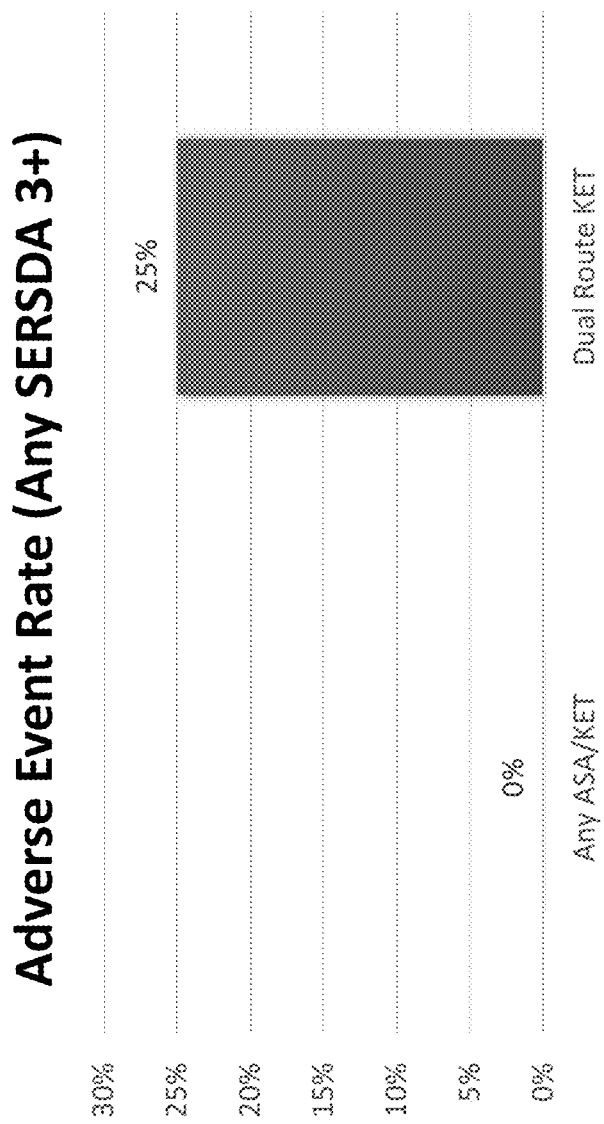
FIG. 4 compares the moderate/severe adverse events experienced in patients of different groups.

It is commonly known that oral ketamine has limited efficacy and, more importantly, ketamine from any route when administered at efficacious doses have side effects limiting outpatient use, and thus a narrow therapeutic window outside of the monitored setting. Accordingly, oral ketamine is not approved for outpatient use. It was further investigated whether a simple combination of oral aspirin and oral ketamine (oral aspirin/ketamine), or a dual route of ketamine (dual route ketamine) would have acceptable safety margin for outpatient use. Unexpectedly, the simple oral aspirin and ketamine administration resulted in a 3.67-point pain reduction (FIG. 7), close to the dual route aspirin/ketamine administration. The dual route ketamine, likewise, reached a 2.75-point reduction (FIG. 6) and only 25% SERSDA3+ adverse even rate (FIG. 4). Such a safety margin is significantly improved as compared to oral ketamine alone.

It is contemplated that such greatly improved efficacy and reduced side effects were at least in part attributed to the dual modes of administration of ketamine, one of which includes intraoral administration for release in the mouth and absorption through the mucosal membrane. The other portion of the ketamine was released in the GI track. The partial intraoral release and partial GI release of ketamine are contemplated to achieve a synergistic effect in increasing the bioavailability and efficacy of ketamine. GI-absorbed ketamine has a different metabolic profile from intraorally absorbed ketamine which directly enters into the blood stream. This is likely due to the first-pass metabolism of the liver for medication absorbed through the GI track.

When administered orally, ketamine undergoes first-pass metabolism, where it is biotransformed in the liver by CYP3A4 (major), CYP2B6 (minor), and CYP2C9 (minor) isoenzymes into norketamine (through N-demethylation) and ultimately dehydronorketamine. Intermediate in the biotransformation of norketamine into dehydronorketamine is the hydroxylation of norketamine into hydroxynorketamine by CYP2B6 and CYP2A6. As the major metabolite of ketamine, norketamine is one-third to one-fifth as potent as an anesthetic, and plasma levels of this metabolite are three times higher than ketamine following oral administration.

Ketamine given directly into the blood stream results in a fast peak of serum ketamine concentration, which immediately begins to drop. The immediate drop is due to the fast metabolism of ketamine into its primary metabolite, norketamine, resulting in high serum levels of norketamine.

Accordingly, the current data suggest that ketamine absorbed directly into the blood stream (such as oral mucosally absorbed) hits a peak serum concentration relatively quickly, within minutes. Ketamine given concurrently through the GI, on the other hand, has a serum peak concentration about 15-20 minutes later. Therefore, when just focusing on the ketamine serum levels, a combination of direct-absorption and GI-absorption will "smooth out" the ketamine serum concentration over time: the direct absorption getting serum levels high early, and the GI absorption keeping serums level high later. This higher and wider serum level of ketamine result in a more pronounced effect.

It is further contemplated that the greatly improved efficacy and reduced side effects of ketamine were also attributed to the combinatory use of ketamine with aspirin. A combination of ketamine and aspirin is contemplated to confer multimodal analgesia, with the contributions of aspirin and ketamine to an opioid sparing effect. It is further contemplated that such effect of aspirin would be observed with other modulators of glutamate ionotropic receptor NMDA type subunit 2A (GRIN2A), such as nicotine, propofol, melatonin, and gangliosides. Gangliosides are sialic acid-containing glycosphingolipids, among which tetrasialoganglioside GQ1b is an example (alpha-N-acetylneuraminosyl-(2→8)-alpha-N-acetylneuraminosyl-(2→3)-beta-D-galactosyl-(1→3)-N-acetyl-beta-D-galactosaminyl-(1→4)-[alpha-N-acetylneuraminosyl-(2→8)-alpha-N-acetylneuraminosyl-(2→3)]-beta-D-galactosyl-(1→4)-beta-D-glucosyl-(1↔1')-N-(octadecanoyl)-sphing-4-enine; PubChem ID: 10887808).

Oral administration of ketamine results in decreased ketamine and increased nor-ketamine concentrations in serum. Consequently, oral ketamine's first-pass effect from hepatic metabolism of ketamine to nor-ketamine may help maintain analgesic potency while simultaneously decreasing side effects when compared to the IV form.

Aspirin is a prototype of non-steroidal anti-inflammatory drugs (NSAIDs), and member of the family of salicylates that have in common salicylic acid as the active agent. The pharmacological properties of aspirin are similar to those of salicylates, but also to the biological actions attributed to salicylate itself, and it has other independent effects due to its reactive acetate group. Both components, salicylate and acetate groups, are biologically active and act independently of each other at different sites. Aspirin is a safe and well-understood non-steroidal anti-inflammatory drug (NSAID). It has certain and clinically accepted analgesic properties. It is a non-selective and irreversible NSAID that inhibits an activity of both cyclooxygenase-1 and 2 and blocks the synthesis of prostaglandins and thromboxanes.

An oral combination drug of aspirin (or another GRIN2A activator such as nicotine, propofol, melatonin and GQ1b) and ketamine (e.g., combination of two administration route) would facilitate the shift from IV opioids to a non-IV therapy for patients with acute MSK pain. This combination has a potential to provide effective analgesia with reduced side effects.

It is contemplated that the synergistic effects between intraoral ketamine and oral ketamine, and between ketamine and aspirin, is applicable to analogs and metabolites of ketamine and other N-methyl-D-aspartate (NMDA) receptor antagonists, and applicable to other NSAIDs.

Example NMDA receptor antagonists include, without limitation, ketamine, dextromethorphan, memantine, and amantadine, as well as opioids methadone, dextropropoxyphene, and ketobemidone. Non-limiting examples of ketamine metabolites include norketamine, hydroxynorketamine (HNK), dehydronorketamine (DHNK), and 6-hydroxyketamine (HK).

Accordingly, one embodiment of the present disclosure provides oral formulations of an NMDA receptor antagonist (e.g., ketamine or a metabolite or analog thereof) suitable/acceptable for outpatient use. In some embodiments, provided is a pharmaceutical composition comprising a first portion comprising a first amount of an NMDA receptor antagonist (e.g., ketamine or a metabolite or analog thereof), and a second portion comprising a second amount of an NMDA receptor antagonist (e.g., ketamine or a metabolite or analog thereof), wherein, upon oral administration to a subject, the first portion disintegrates or dissolves intraorally providing rapid release of the NMDA receptor antagonist of the first portion, and the second portion is substantially more difficult than the first portion to disintegrate or dissolve intraorally but is ingestible and releasable in the gastrointestinal track of the subject.

In one aspect, the NMDA receptor antagonist (e.g., ketamine or a metabolite or analog thereof) of the first portion is at an amount lower than the regular dose of the NMDA receptor antagonist (e.g., 100-400 mg), such as but not limited to, from about 10 mg to about 300 mg. In one aspect, the amount of the NMDA receptor antagonist of the first portion is at least about 10 mg, or least about 20 mg, 30 mg, 40 mg, 50 mg, or 100 mg. In another aspect, the amount of the NMDA receptor antagonist of the first portion is no more than about 50 mg, 75 mg, 100 mg, 125 mg, 150 mg, 175 mg, 200 mg, 225 mg, 250 mg, 275 mg or 300 mg. In one aspect, the NMDA receptor antagonist in the second portion is at an amount lower than the regular dose of the NMDA receptor antagonist (e.g., 100-400 mg), such as but not limited to, from about 10 mg to about 300 mg. In one aspect, the amount of the NMDA receptor antagonist of the first portion is at least about 10 mg, or least about 20 mg, 30 mg, 40 mg, 50 mg, or 100 mg. In another aspect, the amount of the NMDA receptor antagonist of the first portion is no more than about 50 mg, 75 mg, 100 mg, 125 mg, 150 mg, 175 mg, 200 mg, 225 mg, 250 mg, 275 mg or 300 mg.

In one aspect, the NMDA receptor antagonist (e.g., ketamine or a metabolite or analog thereof) of the first portion is at least about 10%, or 20%, or 30%, or 40%, of 50%, or 60%, or 70%, or 80%, or 90% of a therapeutically effective amount. In one aspect, the NMDA receptor antagonist of the first portion is at most about 10%, or 20%, or 30%, or 40%, of 50%, or 60%, or 70%, or 80%, or 90% of a therapeutically effective amount. In one aspect, the NMDA receptor antagonist of the second portion is at least about 10%, or 20%, or 30%, or 40%, of 50%, or 60%, or 70%, or 80%, or 90% of a therapeutically effective amount. In one aspect, the NMDA receptor antagonist of the second portion is at most about 10%, or 20%, or 30%, or 40%, of 50%, or 60%, or 70%, or 80%, or 90% of a therapeutically effective amount.

In one aspect, the first portion of the NMDA receptor antagonist (e.g., ketamine or a metabolite or analog thereof) constitutes at least about 10% of the total NMDA receptor antagonist in the composition. Alternatively, the first portion of the NMDA receptor antagonist constitutes at least about 20%, or 30%, or 40%, or 50%, or 60%, or 70%, or 80%, or 90% of the total NMDA receptor antagonist. In some aspects, however, the first portion of the NMDA receptor antagonist can be less than about 20%, or 30%, or 40%, or 50%, or 60%, or 70%, or 80%, or 90% of the total NMDA receptor antagonist. In a particular aspect, the first portion constitutes from about 40% to about 60%, or alternatively from about 45% to about 55% of the total NMDA receptor antagonist.

In one aspect, the total amount of the NMDA receptor antagonist (e.g., ketamine or a metabolite or analog thereof) in the composition is less than about 50 mg, or 60 mg, or 70 mg, or 80 mg, or 90 mg, or 100 mg, or 120 mg, or 140 mg, or 150 mg, or 160 mg, or 165 mg, or 170 mg, or 180 mg, or 190 mg, 200 mg, 210 mg, 220 mg, 230 mg, 240 mg, 250 mg, 260 mg, 270 mg, 280 mg, 290 mg, or 300 mg. In another aspect, the total amount of the NMDA receptor antagonist in the composition is greater than about 10 mg, 20 mg, or 30 mg, or 40 g, or 50 mg, or 60 mg, or 70 mg, or 80 mg, or 90 mg, or 100 mg, or 110 mg, or 120 mg, or 130 mg, or 140 mg, or 150 mg.

It is further contemplated that the addition of aspirin (or more generally an NSAID) can further enhance the bioavailability and/or efficacy of the NMDA receptor antagonist (e.g., ketamine or a metabolite or analog thereof). In one embodiment, aspirin (or NSAID) is added to the first portion of the NMDA receptor antagonist which disintegrates or dissolves intraorally providing rapid release of the NMDA receptor antagonist of the first portion. In some embodiments, the aspirin in the first portion is at least about 40 mg. In some embodiments, the aspirin in the first portion is at least about 80 mg, 160 mg, 240 mg or 320 mg.

In one embodiment, aspirin is added to the second portion of the NMDA receptor antagonist which is substantially more difficult than the first portion to disintegrate or dissolve intraorally but is ingestible and releasable in the gastrointestinal track of the subject. In some embodiments, the aspirin in the second portion is at least about 40 mg. In some embodiments, the aspirin in the second portion is at least about 80 mg, 160 mg, 240 mg or 320 mg.

Another aspect of the invention provides a process of preparing the disclosed compositions. In some embodiments, the process comprises forming a first portion and a second portion and compressing the first and second portions to form a bilayer or two-halves compressed solid oral dosage form. Preparation of each portion is further described below.

1. First Portion of NMDA Receptor Antagonist for Intraoral Release

Methods of preparing a composition suitable for intraoral release are known in the art. In one aspect, the first portion further includes a film-coating agent, an excipient, a binder, a lubricant, or a plasticizer.

In one aspect, the first portion disintegrates or dissolves intraorally within about 10 minutes. In other aspects, the first portion disintegrates or dissolves intraorally within about 9 minutes, or about 8, or about 7, or about 6, or about 5, or about 4, or about 3 or about 2 minutes, or alternatively about 60 seconds, or about 50, or about 40, or about 30, or about 20, or about 10, or about 5 seconds.

In some aspects, the first portion is chewable. In some aspects, the first portion is in the form of molded triturate.

In one aspect, the first portion further includes an agent that promotes the oral or buccal absorption of the NMDA receptor antagonist. Non-limiting examples of such agents include bile acid salts, sodium lauryl sulfate, lysalbinic acid, salicylic acid, 5-methoxy salicylic acid, 3,4-dihydroxy phenyl acetic acid (DOPAC) and homovanillic acid and their sodium salts thereof. Other hydroxyaryl acids, such as 1-hydroxy-2-naphthoic acid, naphthoresorcyclic acid, ferulic acid, caffeic acid, resorcylic acid and gentisic acid, have similar effects.

The amount of hydroxyaryl or hydroxyaralkyl acid or salt, amide or ester derivatives thereof forms may vary over a wide range; in general, the identity and the amount of the hydroxyaryl or hydroxyaralkyl acids or salt, amide or ester thereof is used in connection with the drug in order to be effective in enhancing the absorption rate of the drug into the bloodstream.

In another aspect, the first portion further includes a disintegrant. Non-limiting examples of disintegrants include crospovidone, crystalline cellulose, hydroxypropylcellulose with a low degree of substitution, croscarmellose sodium, carmellose calcium, carboxystarch sodium, carboxymethyl starch sodium, potato starch, wheat starch, corn starch, rice starch, partly pregelatinized starch, and hydroxypropyl starch. One or two or more of these can be used together. Coating with a disintegrant also contributes to improvement of compression moldability.

2. Second Portion of NMDA Receptor Antagonist, and Optionally Third Portion of Aspirin, for GI Release The second and third portions of the composition can be prepared with methods known in the art for a typical oral dosage form suitable for GI absorption. Like the first portion, the second portion can also include a film-coating agent, an excipient, a binder, a lubricant, or a plasticizer.

Compared to the first portion, the second is substantially more difficult to disintegrate or dissolve intraorally. This can be achieved chemically or physically. For instance, the second portion can be physically harder. In one aspect, the second portion is compressed. In another aspect, the second portion has a hardness that is at least about 10 kilopascal (kp), or alternatively about 11, or 12, or 13, or 14, or 15, or 20, or 25 or 30 or 40 or 50 kp.

Hardness can be assessed by means commonly used in the art, for example, using commercially available hardness testers that are routinely used for assessing the hardness of pharmaceutical dosage forms.

In some aspects, the second portion further comprises a pharmaceutically acceptable flavoring agent not present in the first portion. The flavoring agent provides a flavor that alerts the patients that this portion should not be chewed and needs to be swallowed so as to increase patient compliance.

In one aspect, the NMDA receptor antagonist in the second portion constitutes at least about 10% of the total NMDA receptor antagonist. Alternatively, the NMDA receptor antagonist in the second portion constitutes at least about 20%, or 30%, or 40%, or 50%, or 60%, or 70%, or 80%, or 90% of the total NMDA receptor antagonist. In some aspects, however, the NMDA receptor antagonist in the second portion can be less than about 20%, or 30%, or 40%, or 50%, or 60%, or 70%, or 80%, or 90% of the total NMDA receptor antagonist. In a particular aspect, the NMDA receptor antagonist in second portion constitutes from about 40% to about 60%, or alternatively from about 45% to about 55% of the total NMDA receptor antagonist. In one aspect, the ratio of the NMDA receptor antagonist between the first portion and the second portion is about 1:1. Alternatively, the ratio is at least about 1:4, or 1:3, or 1:2 or 1:1.5, or is no more than about 4:1, 3:1, 2:1 or 1.5:1.

The pharmaceutical composition of the present disclosure can be in the form of a tablet or capsule. When in the form of a tablet, the second portion, in one aspect, is enclosed within the first portion or alternatively partially exposed.

When the composition is in the form of a tablet, the tablet can include an outer portion and an inter portion, with the outer portion containing the first portion and the inner portion containing the second portion and optionally the third portion.

In one aspect, the outer portion is formulated to dissolve in the oral cavity of a subject and to release the NMDA receptor antagonist in the first portion across the oral mucosa of the subject. In one aspect, the inner portion is harder than the outer portion and is formulated for dissolving in stomach, intestines, or further distal in the gastrointestinal tract of the subject.

In one aspect, the inner portion comprises a texture on the surface that is recognizable by the tongue of a subject. In another aspect, the outer portion comprises a water soluble sugar or sugar substitute. In another aspect, the outer portion is surrounded by a thin shell to allow encapsulation of liquid, powder or gel in the outer portion.

In one aspect, the outer portion is flavored or sweetened. In one aspect, the tablet further comprises an intermediate layer between the outer and inner portions. In one aspect, the intermediate layer comprises enteric coating. In one aspect, the inner portion is formulated to absorb a biting shock and not break a tooth. In another aspect, the tablet comprises a layer of ketamine which breaks down in the mouth, but this layer has particles within it that don't completely break down in the mouth and stay full particles, such that there is partial intraoral release and, when the particles as swallowed, partial gastrointestinal release.

The pharmaceutical composition of the above embodiments can further include a third portion that comprises an effective amount of aspirin. In one aspect, the third portion is in the form of controlled release. In another aspect, the third portion further comprises enteric coating. In yet another aspect, the third portion is enclosed in the first portion or the second portion.

3. Combination of NMDA Receptor Antagonist and GRIN2A Modulator

Another discovery of the present disclosure is that certain desired effects of an NMDA receptor antagonist (e.g., ketamine or a metabolite or analog thereof), such as pain reduction, suppression of depression, reduction of fatigue, can be further enhanced by co-administration with aspirin. The co-administration of aspirin, or another GRIN2A modulator, is also associated with a reduction of the undesired effects of the NMDA receptor antagonist, including its sedation effect and addiction potential.

In accordance with one embodiment of the disclosure, provided is a pharmaceutical composition comprising an NMDA receptor antagonist (e.g., ketamine or a metabolite or analog thereof) and a glutamate ionotropic receptor NMDA type subunit 2A (GRIN2A) modulator. In some embodiments, the GRIN2A modulator is an activator. Non-limiting examples include aspirin, nicotine, propofol, melatonin and GQ1b.

In some embodiments, the NMDA receptor antagonist in the composition is provided as two portions, with the first portion comprising a first amount of the NMDA receptor antagonist, and a second portion comprising a second amount of the NMDA receptor antagonist, wherein, upon oral administration to a subject, the first portion disintegrates or dissolves intraorally providing rapid release of the NMDA receptor antagonist of the first portion, and the second portion is substantially more difficult than the first portion to disintegrate or dissolve intraorally but is ingestible and releasable in the gastrointestinal track of the subject.

In some embodiments, the GRIN2A modulator is formulated together with the first portion of the NMDA receptor antagonist. In some embodiments, the GRIN2A modulator is formulated together with the second portion of the NMDA receptor antagonist. In some embodiments, the GRIN2A modulator is formulated together with each of the first portion and the second portion of the NMDA receptor antagonist.

In another embodiment, the present disclosure provides a pharmaceutical composition comprising an NMDA receptor antagonist and aspirin. Either or both of the NMDA receptor antagonist and aspirin can be formulated for both intraoral and oral administration, as described throughout.

In some embodiments, the NMDA receptor antagonist (e.g., ketamine or a metabolite or analog thereof) is at an amount lower than the regular dose of the NMDA receptor antagonist (e.g., 100-400 mg), such as but not limited to, from about 20 mg to about 300 mg. In one aspect, the amount of the NMDA receptor antagonist of the first portion is at least about 20 mg, or least about 30 mg, 40 mg, 50 mg, or 100 mg. In another aspect, the amount of the NMDA receptor antagonist of the first portion is no more than about 50 mg, 75 mg, 100 mg, 125 mg, 150 mg, 175 mg, 200 mg, 225 mg, 250 mg, 275 mg or 300 mg.

In some embodiments, the composition includes two portions of aspirin, a first portion containing a first amount of the aspirin, and a second portion containing a second amount of the aspirin. Upon oral administration to a subject, the first portion disintegrates or dissolves intraorally providing rapid release of the aspirin of the first portion, and the second portion is substantially more difficult than the first portion to disintegrate or dissolve intraorally but is ingestible and releasable in the gastrointestinal track of the subject.

4. Additional Additives to the Compositions

In yet another aspect, either or both of the first portion and second portion further comprises excipients, lubricants, pH adjusters, taste-masking agents, sweeteners, acidifiers, refrigerants, foaming agents, preservatives, fluidizers, antioxidants, colorants, stabilizers, surfactants, buffering agents, flavors, binders or drug solubilizers. A person skilled in the art may immediately list specific examples of these additives.

Any excipient used for pharmaceutical preparations can be used without limitation, but examples of excipients used in the tablet of the present invention can include sugars such as erythritol, mannitol, xylitol, sorbitol, lactitol, paratinit, paratinose, maltitol, maltose, trehalose, lactose, sucrose, glucose, olygosaccharides, fructose and maltose and the like. One or two or more kinds of these excipients can be used.

Various embodiments of the composition may include pharmaceutically acceptable binders (adhesives). Binders are agents that impart cohesive properties to powdered materials through particle-particle bonding. Examples of suitable binders include celluloses and crosslinked polyvinyl pyrrolidone, matrix binders (dry starch, dry sugars), film binders (polyvinyl pyrrolidone (PVP), starch paste, celluloses, bentonite, sucrose), and chemical binders (polymeric cellulose derivatives, such as carboxy methyl cellulose, hydroxypropylcellulose (HPC) and hydroxypropylmethylcellulose (HPMC); sugar syrups; corn syrup; water soluble polysaccharides such as acacia, tragacanth, guar and alginates; gelatin; gelatin hydrolysate; agar; sucrose; dextrose; and non-cellulosic binders, such as polyvinyl pyrrolidone, polyethylene glycol (PEG), vinyl pyrrolidone copolymers, pregelatinized starch, sorbitol, glucose, microcrystalline cellulose, such as FMC BioPolymer's Avicel® PH101 and Avicel® PH102, and silicified microcrystalline cellulose, such as Penwest Pharmaceutical's ProSolv SMCC™). In specific embodiments, a binder is selected from the group consisting of corn starch, potato starch, polyvinyl pyrrolidone, hydroxypropylmethyl cellulose, and hydroxylpropyl cellulose. A binder may be included in any portion of the dosage form, such as the intragranular portion and/or extragranular portion of either or both of the first and second layers.

In some embodiments, the composition further comprises a pharmaceutically acceptable diluent or filler. Pharmaceutically acceptable diluents include, but are not limited to, lactose (such as lactose monohydrate, lactose anhydrous, and DMV International's Pharmatose® DCL21 crystalline alpha monohydrate milled lactose), mannitol, talc, magnesium stearate, sodium chloride, potassium chloride, citric acid, spray-dried lactose, starch, hydrolyzed starches, directly compressible starch, microcrystalline cellulose (such as Avicel® PH101 and Avicel® PH102), cellulosics, sorbitol, sucrose, glucose, sucrose-based materials, saccharides, calcium sulfate, dibasic calcium phosphate (such as Emcompress®) and dextrose, and/or mixtures of any of the foregoing. In specific embodiments, a diluent is selected from the group consisting of microcrystalline cellulose, lactose, mannitol, dicalcium phosphate, dextrose, compressible sugar, and spray-dried lactose with microcrystalline cellulose. A diluent may be may be included in any portion of the dosage form, such as the intragranular portion and/or extragranular portion of either or both of the first and second layers.

In some embodiments, the composition comprises magnesium stearate. In specific embodiments, the magnesium stearate is present in a range of about 0.5% to 2% w/w, based on the total weight of the layer.

In some embodiments, the diluent is microcrystalline cellulose or microlac (spray-dried lactose with microcrystalline cellulose). In specific embodiments, the microcrystalline cellulose or microlac is present in a range of about 20% to 60% w/w, based on the total weight of the layer.

Various embodiments of the invention may include pharmaceutically acceptable anti-adherents (anti-sticking agents, glidants, flow promoters, lubricants) such as talc, colloidal silicon dioxide, such as Aerosil® 200, magnesium stearate, fumed silica (Carbosil, Aerosil), micronized silica (Syloid No. FP 244, Grace U.S.A.), polyethylene glycols, surfactants, waxes, stearic acid, stearic acid salts, stearic acid derivatives, calcium stearate, silica gel, starch, hydrogenated vegetable oils, sodium benzoate, sodium acetate, leucine, PEG-4000, and magnesium lauryl sulfate. In specific embodiments, an anti-adherents is selected from glidants and lubricants. Suitable glidants include, but are not limited to, colloidal silicon dioxide (Aerosil®), magnesium trisilicate, talc, and tribasic calcium phosphate. Suitable lubricants include, but are not limited to magnesium, aluminum, calcium, zinc stearate, and talc. An anti-adherent may be included in any portion of the dosage form, such as the intragranular portion and/or extragranular portion of either or both of the first and second layers. In specific embodiments, an anti-adherent is included in the extragranular portion of the first layer and/or the extragranular portion of the second layer.

In some embodiments, the glidant is talc. In specific embodiments, talc is present in a range of about 1% to 7% w/w, based on the total weight of each layer.

C. Therapeutic Methods

Therapeutic methods are also provided. In one aspect, provided is a method of administering ketamine to a subject with improved efficacy or bioavailability, comprising administering to the subject (a) a first composition comprising a first amount of ketamine and (b) a second composition comprising a second amount of ketamine, wherein the first composition disintegrates or dissolves intraorally providing rapid release of the ketamine of the first portion, and the second composition is ingested and released in the gastrointestinal track of the subject.

In one aspect, the ketamine of the first composition is at an amount lower than the regular dose of ketamine (e.g., 10-400 mg), such as but not limited to, from about 10 mg to about 300 mg. In one aspect, the amount of ketamine of the first composition is at least about 10 mg, or least about 20 mg, 30 mg, 40 mg, 50 mg, or 100 mg. In another aspect, the amount of ketamine of the first composition is no more than about 50 mg, 75 mg, 100 mg, 125 mg, 150 mg, 175 mg, 200 mg, 225 mg, 250 mg, 275 mg or 300 mg. In one aspect, the ketamine in the second composition is at an amount lower than the regular dose of ketamine (e.g., 100-400 mg), such as but not limited to, from about 10 mg to about 300 mg. In one aspect, the amount of ketamine of the first composition is at least about 10 mg, or least about 20 mg, 30 mg, 40 mg, 50 mg, or 100 mg. In another aspect, the amount of ketamine of the first composition is no more than about 50 mg, 75 mg, 100 mg, 125 mg, 150 mg, 175 mg, 200 mg, 225 mg, 250 mg, 275 mg or 300 mg.

In one aspect, the ketamine of the first composition is at least about 10%, or 20%, or 30%, or 40%, of 50%, or 60%, or 70%, or 80%, or 90% of a therapeutically effective amount. In one aspect, the ketamine of the first composition is at most about 10%, or 20%, or 30%, or 40%, of 50%, or 60%, or 70%, or 80%, or 90% of a therapeutically effective amount. In one aspect, the ketamine of the second composition is at least about 10%, or 20%, or 30%, or 40%, of 50%, or 60%, or 70%, or 80%, or 90% of a therapeutically effective amount. In one aspect, the ketamine of the second composition is at most about 10%, or 20%, or 30%, or 40%, of 50%, or 60%, or 70%, or 80%, or 90% of a therapeutically effective amount.

In one aspect, the first composition of ketamine constitutes at least about 10% of the total ketamine administered. Alternatively, the first composition of ketamine constitutes at least about 20%, or 30%, or 40%, or 50%, or 60%, or 70%, or 80%, or 90% of the total ketamine. In some aspects, however, the first composition of ketamine can be less than about 20%, or 30%, or 40%, or 50%, or 60%, or 70%, or 80%, or 90% of the total ketamine. In a particular aspect, the first composition constitutes from about 40% to about 60%, or alternatively from about 45% to about 55% of the total ketamine.

In one aspect, the total amount of ketamine administered is less than about 50 mg, or 60 mg, or 70 mg, or 80 mg, or 90 mg, or 100 mg, or 120 mg, or 140 mg, or 150 mg, or 160 mg, or 165 mg, or 170 mg, or 180 mg, or 190 mg, 200 mg, 210 mg, 220 mg, 230 mg, 240 mg, 250 mg, 260 mg, 270 mg, 280 mg, 290 mg, or 300 mg. In another aspect, the total amount of ketamine administered is greater than about 10 mg, 20 mg, or 30 mg, or 40 g, or 50 mg, or 60 mg, or 70 mg, or 80 mg, or 90 mg, or 100 mg, or 110 mg, or 120 mg, or 130 mg, or 140 mg, or 150 mg.

Also provided, in one embodiment, is a method for treating acute pain in a patient, comprising orally administering an effective amount of ketamine to the patient.

The effective amount may be at least 0.1 mg/kg, or at least 0.2 mg/kg, 0.3, 0.35, 0.4, 0.45, 0.5, 0.55, 0.6, 0.65, 0.7, 0.75, 0.8, 0.85, 0.9, 0.95 or 1 mg/kg. In some embodiments, the effective amount is not greater than 2 mg/kg, or not greater than 1.9 mg/kg, 1.85, 1.8, 1.75, 1.7, 1.65, 1.6, 1.55, 1.5, 1.45, 1.4, 1.35, 1.3, 1.25, 1.2, 1.15, 1.1, 1.05, 1, 0.95, 0.9, 0.85, 0.8, 0.75, 0.7, 0.65, 0.6, 0.55, or 0.5 mg/kg. In some embodiments, the effective amount is from 0.3 mg/kg to 0.8 mg/kg, preferably from 0.4 mg/kg to 0.6 mg/kg, and more preferably 0.5 mg/kg.

Also provided, in one embodiment, is a method for treating acute on chronic headache in a patient, comprising orally administering an effective amount of ketamine to the patient.

The effective amount may be at least 0.1 mg/kg, or at least 0.2 mg/kg, 0.3, 0.35, 0.4, 0.45, 0.5, 0.55, 0.6, 0.65, 0.7, 0.75, 0.8, 0.85, 0.9, 0.95 or 1 mg/kg. In some embodiments, the effective amount is not greater than 2 mg/kg, or not greater than 1.9 mg/kg, 1.85, 1.8, 1.75, 1.7, 1.65, 1.6, 1.55, 1.5, 1.45, 1.4, 1.35, 1.3, 1.25, 1.2, 1.15, 1.1, 1.05, 1, 0.95, 0.9, 0.85, 0.8, 0.75, 0.7, 0.65, 0.6, 0.55, or 0.5 mg/kg. In some embodiments, the effective amount is from 0.5 mg/kg to 1.5 mg/kg, preferably from 0.7 mg/kg to 1 mg/kg, and more preferably 0.85 mg/kg.

Also provided, in one embodiment, is a method for treating depression in a patient, comprising orally administering an effective amount of ketamine to the patient.

The effective amount may be at least 0.1 mg/kg, or at least 0.2 mg/kg, 0.3, 0.35, 0.4, 0.45, 0.5, 0.55, 0.6, 0.65, 0.7, 0.75, 0.8, 0.85, 0.9, 0.95 or 1 mg/kg. In some embodiments, the effective amount is not greater than 2 mg/kg, or not greater than 1.9 mg/kg, 1.85, 1.8, 1.75, 1.7, 1.65, 1.6, 1.55, 1.5, 1.45, 1.4, 1.35, 1.3, 1.25, 1.2, 1.15, 1.1, 1.05, 1, 0.95, 0.9, 0.85, 0.8, 0.75, 0.7, 0.65, 0.6, 0.55, or 0.5 mg/kg. In some embodiments, the effective amount is from 0.75 mg/kg to 1.75 mg/kg, preferably from 1 mg/kg to 1.5 mg/kg, and more preferably 1.2 mg/kg.

Also provided, in one embodiment, is a method for treating cannabinoid hyperemesis syndrome exacerbations in a patient, comprising orally administering an effective amount of ketamine to the patient.

The effective amount may be at least 0.1 mg/kg, or at least 0.2 mg/kg, 0.3, 0.35, 0.4, 0.45, 0.5, 0.55, 0.6, 0.65, 0.7, 0.75, 0.8, 0.85, 0.9, 0.95 or 1 mg/kg. In some embodiments, the effective amount is not greater than 2 mg/kg, or not greater than 1.9 mg/kg, 1.85, 1.8, 1.75, 1.7, 1.65, 1.6, 1.55, 1.5, 1.45, 1.4, 1.35, 1.3, 1.25, 1.2, 1.15, 1.1, 1.05, 1, 0.95, 0.9, 0.85, 0.8, 0.75, 0.7, 0.65, 0.6, 0.55, or 0.5 mg/kg. In some embodiments, the effective amount is from 0.2 mg/kg to 1 mg/kg, preferably from 0.2 mg/kg to 0.6 mg/kg, and more preferably 0.4 mg/kg. It is further contemplated that the addition of an GRIN2A modulator, e.g., aspirin, can further enhance the bioavailability and/or efficacy of the ketamine.

In accordance with one embodiment of the disclosure, provided is a method of administering ketamine to a subject with improved efficacy or bioavailability, or reduced side effects, comprising administering to the subject ketamine and a glutamate ionotropic receptor NMDA type subunit 2A (GRIN2A) modulator. In some embodiments, the GRIN2A modulator is an activator. Non-limiting examples include aspirin, nicotine, propofol, melatonin and GQ1b.

In some embodiments, the ketamine is provided as two portions or two compositions, with the first portion/composition comprising a first amount of ketamine, and a second portion/composition comprising a second amount of ketamine, wherein, upon oral administration to a subject, the first portion/composition disintegrates or dissolves intraorally providing rapid release of the ketamine of the first portion, and the second portion/composition is substantially more difficult than the first portion to disintegrate or dissolve intraorally but is ingestible and releasable in the gastrointestinal track of the subject.

In some embodiments, the GRIN2A modulator is absorbed intraorally. In some embodiments, the GRIN2A modulator is absorbed in the GI track. In some embodiments, the GRIN2A modulator is partially absorbed intraorally and partially absorbed in the GI track.

In some embodiments, the GRIN2A modular is aspirin. In one embodiment, aspirin is administered in a manner that disintegrates or dissolves intraorally providing rapid release of the ketamine of the first composition. In some embodiments, the aspirin so administered is at least about 40 mg. In some embodiments, the aspirin is at least about 80 mg, 160 mg, 240 mg or 320 mg.

In one embodiment, aspirin is administered such that it is substantially more difficult than the first composition to disintegrate or dissolve intraorally but is ingestible and releasable in the gastrointestinal track of the subject. In some embodiments, the aspirin so administered is at least about 40 mg. In some embodiments, the aspirin so administered is at least about 80 mg, 160 mg, 240 mg or 320 mg.

It is also contemplated that a single composition of ketamine can also be used to achieve the desired effect, when a portion of the ketamine is dissolved intraorally and the remaining is released in the GI track. Such a composition of ketamine can be combined with aspirin, as disclosed above.

Thus, also provided is a method of administering ketamine to a subject in need of treating a disease or condition, comprising administering to the subject a therapeutically effective amount of ketamine, wherein a portion of the ketamine disintegrates or dissolves intraorally within 10 minutes permitting rapid release of the ketamine in the portion, and the remaining ketamine is ingested and released in the gastrointestinal track of the subject.

The disease or condition, without limitation, can be pain, asthma, or depression. In some embodiments, the subject is need of anesthesia.

In some aspects, the first composition or portion of the ketamine disintegrates or dissolves intraorally within about 9 minutes, or about 8, or about 7, or about 6, or about 5, or about 4, or about 3 or about 2 minutes, or alternatively about 60 seconds, or about 50, or about 40, or about 30, or about 20, or about 10, or about 5 seconds. In any embodiment of the above methods, the method further comprises administering to the subject an effective amount of aspirin.

Also provided, in one embodiment, is a method of administering ketamine to a subject, comprising administering to the subject ketamine and aspirin.

In some embodiments, the aspirin is administered as (a) a first composition comprising a first amount of aspirin and (b) a second composition comprising a second amount of aspirin, wherein the first composition disintegrates or dissolves intraorally providing rapid release of the aspirin of the first portion, and the second composition is ingested and released in the gastrointestinal track of the subject. In some embodiments, the ketamine is administered as (a) a first composition comprising a first amount of ketamine and (b) a second composition comprising a second amount of ketamine, wherein the first composition disintegrates or dissolves intraorally providing rapid release of the ketamine of the first portion, and the second composition is ingested and released in the gastrointestinal track of the subject.

In some embodiments, the ketamine is at an amount lower than the regular dose of ketamine (e.g., 10-400 mg), such as but not limited to, from about 20 mg to about 300 mg. In one aspect, the amount of ketamine of the first portion is at least about 20 mg, or least about 30 mg, 40 mg, 50 mg, or 100 mg. In another aspect, the amount of ketamine of the first portion is no more than about 50 mg, 75 mg, 100 mg, 125 mg, 150 mg, 175 mg, 200 mg, 225 mg, 250 mg, 275 mg or 300 mg.

The administration of ketamine can be useful for treating certain diseases or conditions, such as pain, asthma, or depression. In some embodiments, the subject is need of anesthesia.

Example 1. Dual-Route Ketamine and Aspirin in Musculoskeletal Pain Reduction This example evaluates analgesic efficacy of dual-route ketamine (liquid intraoral ketamine+oral ketamine) taken simultaneously with dual-route aspirin (intraoral aspirin+oral aspirin) for pain management of adult emergency department (ED) patients presenting to the ED with acute musculoskeletal pain.

It is contemplated that the treatment will result in analgesia with a change in pain score at least of 1.3 points on numeric rating pain scale (NRS). The primary outcome of this test is the reduction in participant's pain scores at 60 minutes post medication administration.

Subjects: Patients 18 years of age and older presenting to the ED with acute musculoskeletal painful conditions (traumatic and non-traumatic) with an initial pain score of 5 or more on a standard 11-point (0 to 10) numeric rating scale and requiring oral analgesia as determined by the treating attending physician. Study investigators and research assistants will perform patients' screening and enrollment. All patients will be enrolled at various times of the day when study investigators will be available for patient enrollment and an ED pharmacist will be available for medication preparation.

Eligibility Criteria: Patients 18 years of age and older presenting to the ED with acute musculoskeletal painful conditions (traumatic and non-traumatic) with an initial pain score of 5 on a standard 11-point (0 to 10) numeric rating scale. Patients will be awake, alert, oriented to person, place, and time, and will be able to demonstrate understanding of the informed consent process and content. Patients also will have to demonstrate ability to verbalize the nature of any adverse effects they might experience as well as to express their pain severity by using the NRS.

Exclusion Criteria: Patients with: altered mental status, allergy to aspirin and ketamine, pregnant patients, unstable vital signs (systolic blood pressure <90 or >180 mm Hg, pulse rate <50 or >150 beats/min, and respiration rate <10 or >30 breaths/min), inability to provide consent, consumption of Aspirin or NSAID's within 6 hours of arrival to the ED, active PUD, history of GI Hemorrhage, history of renal and hepatic insufficiency, past medical history of alcohol or drug abuse, or schizophrenia.

Design: This is a prospective observational pilot trail evaluating analgesic efficacy and safety of dual-route ketamine in adult patients presenting to the ED of Maimonides Medical Center with acute musculoskeletal painful conditions. Upon meeting the eligibility criteria, patients will be offered to participate in the study.

Data Collection Procedures: Each patient will be approached by a study investigator for acquisition of written informed consent and Health Insurance Portability and Accountability Act authorization after being evaluated by the treating emergency physician and determined to meet study eligibility criteria. When English is not the participant's primary language, a language-appropriate consent form will be used and non-investigator, hospital-employed, trained interpreters or licensed telephone interpreter will assist in acquisition of informed consent. Baseline pain score will be determined with an 11-point numeric rating scale (0 to 10), described to the patient as "no pain" being 0 and "the worst pain imaginable" being 10. A study investigator will record the patient's body weight and baseline vital signs.

The on-duty ED pharmacist will prepare an oral dose of ketamine by using a formulary for parenteral use. The oral dosing regimen of ketamine is 0.5 mg/kg that will be placed in the syringe or a medication cup and sweetener (Ora-Sweet®) will be added to offset unpleasant taste of the ketamine. The total dose for aspirin is 325 mg as specified by the sponsor. The research associate will deliver both medications (dual-route aspirin and dual-route ketamine) to the patients' nurse. Study investigators will record pain scores and adverse effects at 15, 30, 60, 90, and 120 minutes. If patients reported a pain numeric rating scale score of 5 or greater and requested additional pain relief, an oral immediate release morphine tablet of 7.5 mg will be given.

All data will be recorded on data collection sheets, including patients' sex, demographics, medical history, and vital signs, and entered into SPSS (version 24.0; IBM Corp) by the research manager. The statistician, who will work independently of any data collection, will conduct statistical analyses.

Patients will be closely monitored for adverse effects during the entire study period (up to 120 minutes) by study investigators. Common adverse effects that are associated with oral ketamine are felling of unreality, dizziness, nausea, vomiting, and sedation. Common adverse effects are associated with dual-route aspirin are nausea, dyspepsia, epigastric discomfort.

Data Analysis: Data analyses will include frequency distributions and independent-sample t-test to assess differences in pain scores at the various intervals. Mixed-model linear regression will be used to compare changes in pain on numeric rating scale across time points.

For categorical outcomes (e.g., complete resolution of pain), $X^2$ or Fisher's exact test will be used to compare outcomes at 60 minutes. Based on the validation of a verbally administered rating scale of acute pain in the ED and the comparison of verbal and visual pain scales, this example will use a primary outcome consisting of a minimal clinically meaningful difference of 1.3 between three groups at the 60-minute pain assessment.

Sample Size: Assuming a minimal clinically meaningful difference of 1.3 in change of pain score from the baseline until 60 minutes, given a standard deviation of 3.0, with a one-side 97.5% confidence interval, this example will need 21 subjects for this pilot trial. This example would enroll 25 patients to account for any loss to follow-up.

Expected Outcomes: The primary outcome will include a reduction of pain scores on numeric rating pain scale (NRS) at 60 minutes mark form the baseline. The secondary outcomes will include a need for rescue analgesia and rates of adverse up to 90 minutes. With respect to unique adverse effects of SDK, this example will use Side Effect Rating Scale for Dissociative Anesthetics (SERSDA) and Richmond Agitation Sedation Scale (RASS). SERSDA Scale includes fatigue, dizziness, nausea, headache, feeling of unreality, changes in hearing, mood change, general discomfort, and hallucinations with severity of each graded by patients on a five-point scale, with "0" representing the absence of any adverse effects and "4" representing a severely bothersome side effect. RASS evaluates the severity of agitation and/or sedation in accordance to the nine-point scale with scores ranging from "-4" (deeply sedated) to "0" (alert and calm) to "+4" (combative).

Adverse Events: Dizziness, nausea, vomiting, agitation and or sedation, weakness or fatigue, feelings of unreality, epigastric pain, dyspepsia.

SAE Reporting: Any serious adverse event, requiring intervention, will be reported to the IRB within 24 hours of discovery by the research staff. Less serious adverse events will be reported within a week of discovery. There are known expected outcomes and side effects to the procedures and medications being received and these are the same risks/side effects as the standard of care—these will be reported if they are serious and require intervention.

Timetable: The entire study (from commencement until recruitment of the last patient) will last 12 months. The research team will monitor and record each patient's pain scores and adverse events. The research team, pharmacist, and research manager will be immediately aware and/or notified if a serious adverse event occurs. ED team of physicians and nurses will treat the patient appropriately, and subsequently the adverse effect report will be filed to the IRB.

Example 2. Comparison of Ketamine/Aspirin with Ketamine Alone

This example compares dual-route ketamine (oral+intraoral) to oral ketamine alone plus oral aspirin alone in adult patients presenting to the ED with acute musculoskeletal pain, in a randomized, double-blind, clinical trial.

Oral formulations of ketamine are not commercially available. The parenteral formulation is given as an oral solution by using an injectable vial. The oral bioavailability of ketamine, defined as area under plasma concentration time curve (AUC), after a single oral dose of 0.5 mg/kg is about one fifth of the availability after an intravenous injection. In a ketamine-naive patient, oral administration of ketamine can start with a single dose of 0.5 mg/kg ketamine racemic mixture or 0.25 mg/kg S-ketamine to evaluate the effect on pain relief and the duration of effect.

Doses can be increased in steps of 0.5 or 0.25 mg/kg according to the efficacy and adverse effects, respectively. The average dosing frequency of 3-4 times daily found in the clinical studies corresponds well with the elimination half-lives of ketamine (2-3 h) and nor-ketamine (4 h). The conversion from parenteral to oral administration in an equipotent dose is complex and is not solely based on a reduced bioavailability. The median conversion rate from subcutaneous to oral ketamine used in the case reports was 1:1.

The primary outcome of this trial is the comparative reduction in participant's pain scores at 60 minutes post-medication administration.

Example Arms and Interventions

| Arms | Assigned Intervention |
| --- | --- |
| Ketamine + Aspirin | 0.5 mg/kg of ketamine (oral) + 324 mg of aspirin (oral) |
| Ketamine alone (dual-route) | 0.5 mg/kg of ketamine (oral + intraoral) |

Subjects: Patients 18 years of age and older presenting to the ED with acute musculoskeletal painful conditions (traumatic and non-traumatic) with an initial pain score of 5 or more on a standard 11-point (0 to 10) numeric rating scale and requiring oral analgesia as determined by the treating attending physician. Patients' screening and enrollment will be performed by study investigators and research assistants. All patients will be enrolled at various times of the day when study investigators will be available for patient enrollment and an ED pharmacist will be available for medication preparation.

Eligibility Criteria: Patients 18 years of age and older presenting to the ED with acute musculoskeletal painful conditions (traumatic and non-traumatic) with an initial pain score of 5 on a standard 11-point (0 to 10) numeric rating scale. Patients will have to be awake, alert, and oriented to person, place, and time, and will be able to demonstrate understanding of the informed consent process and content. Patients also will have to demonstrate ability to verbalize the nature of any adverse effects they might experience as well as to express their pain severity by using the NRS.

Exclusion Criteria: Patients with altered mental status, allergy to aspirin and ketamine, pregnant patients, unstable vital signs (systolic blood pressure <90 or >180 mm Hg, pulse rate <50 or >150 beats/min, and respiration rate <10 or >30 breaths/min), inability to provide consent, consumption of Aspirin or NSAID's within 6 hours of arrival to the ED, active PUD, history of GI Hemorrhage, history of renal and hepatic insufficiency, past medical history of alcohol or drug abuse, or schizophrenia.

Design: This is a prospective, randomized, double-blind trial comparing analgesic efficacy and safety of the treatments in patients presenting to the ED of Maimonides Medical Center with acute musculoskeletal pain. Upon meeting the eligibility criteria, patients will be randomized into one of the two study arms: 325 mg dual-route aspirin+1 mg/kg oral ketamine, and oral ketamine alone at 1 mg/kg.

Data Collection Procedures: Each patient will be approached by a study investigator for acquisition of written informed consent and Health Insurance Portability and Accountability Act authorization after being evaluated by the treating emergency physician and determined to meet study eligibility criteria. When English is not the participant's primary language, a language-appropriate consent form will be used and non-investigator, hospital-employed, trained interpreters or licensed telephone interpreter will assist in acquisition of informed consent. Baseline pain score will be determined with an 11-point numeric rating scale (0 to 10), described to the patient as "no pain" being 0 and "the worst pain imaginable" being 10. A study investigator will record the patient's body weight and baseline vital signs. All data will be recorded on data collection sheets, including patients' sex, demographics, medical history, and vital signs, and entered into SPSS (version 24.0; IBM Corp) by the research manager. Confirmation of written consent acquisition for all participants, and statistical analyses will be conducted by the statistician (Michael Silver), who will work independently of any data collection.

The on-duty ED pharmacist will prepare an oral dose of ketamine by using an injectable form for parenteral use. The on-duty ED pharmacist will prepare a syringe/medication cup containing: the combo group (Combo): 325 mg and 0.5 or 1 mg/kg oral dose ketamine; oral ketamine (OK) group: matching placebo tablets and 0.5 or 1 mg/kg oral dose ketamine according to the predetermined randomization list, which will be created in SPSS (version 24; IBM Corp, Armonk, N.Y.) with block randomization of every 10 participants. The research associate will deliver syringes/medication cups to the patients' nurse who will administer medication. Study investigators will record pain scores and adverse effects at 30, 60, 90, and 120 minutes. If patients reported a pain numeric rating scale score of 5 or greater and requested additional pain relief, an oral immediate release morphine tablet of 7.5 mg will be given. Patients will be closely monitored for adverse effects during the entire study period (up to 120 minutes) by study investigators. Common adverse effects that are associated with OK are felling of unreality, dizziness, nausea, vomiting, and sedation. Common adverse effects are associated with Combo are nausea, dyspepsia, epigastric discomfort, heartburn, dizziness.

Data Analysis: Data analyses will include frequency distributions and independent-sample t-test to assess differences in pain scores at the various intervals. Mixed-model linear regression will be used to compare changes in pain numeric rating scale across time points.

For categorical outcomes (e.g., complete resolution of pain), a $X^2$ or Fisher's exact test will be used to compare outcomes at 60 minutes. Based on the validation of a verbally administered rating scale of acute pain in the ED and the comparison of verbal and visual pain scales, we will use a primary outcome consisting of a minimal clinically meaningful difference of 2 between two groups at the 60-minute pain assessment.

Contemplated Outcomes: The primary outcome will include a reduction of pain scores on numeric rating pain scale (NRS) at 60 minutes mark form the baseline. The secondary outcomes will include a need for rescue analgesia and rates of adverse up to 120 minutes. With respect to unique adverse effects of SDK, we will use Side Effect Rating Scale for Dissociative Anesthetics (SERSDA) and Richmond Agitation Sedation Scale (RASS) (ref) SERSDA Scale includes fatigue, dizziness, nausea, headache, feeling of unreality, changes in hearing, mood change, general discomfort, and hallucinations with severity of each graded by patients on a five-point scale, with "0" representing the absence of any adverse effects and "4" representing a severely bothersome side effect. RASS evaluates the severity of agitation and/or sedation in accordance to the nine-point scale with scores ranging from "−4" (deeply sedated) to "0" (alert and calm) to "+4" (combative).

SAE Reporting: Any serious adverse event, requiring intervention, will be reported to the IRB within 24 hours of discovery by the research staff. Less serious adverse events will be reported within a week of discovery. There are known expected outcomes and side effects to the procedures and medications being received and these are the same risks/side effects as the standard of care—these will be reported if they are serious and require intervention.

Timetable: The entire study (from commencement until recruitment of the last patient) will last 12 months. The research team will monitor and record each patient's pain scores and adverse events. The research team, pharmacist, and research manager will be immediately aware and/or notified if a serious adverse event occurs. The patient will be treated appropriately by ED team of physicians and nurses, and subsequently the adverse effect report will be filed to the IRB.

Example 3. Management of Headache

This example compares the combination of dual-route aspirin and dual-route ketamine to Rimegepant (Nurtec®, Biohaven Pharmaceuticals, New Haven, Conn.) for managing acute headache in the ED in a randomized, open-label, clinical trial.

Nurtec (Rimegepant) is an orally administered small molecule CGRP receptor antagonist with efficacy in the acute treatment of migraine. Following oral administration of NURTEC Orally Disintegrating Tablet, rimegepant is absorbed with the maximum concentration at 1.5 hours. The absolute oral bioavailability of rimegepant is approximately 64%. Rimegepant is primarily metabolized by CYP3A4 and to a lesser extent by CYP2C9. Rimegepant is primarily eliminated in unchanged form (~77% of the dose) with no major metabolites (i.e., >10%) detected in plasma. The most common adverse reaction are nausea (2% in patients who received NURTEC ODT compared to 0.4% of patients who received placebo). Hypersensitivity, including dyspnea and severe rash, occurred in less than 1% of patients treated with NURTEC ODT.

NURTEC ODT 75 mg orally disintegrating tablets are white to off-white, circular, debossed with the symbol, and supplied in cartons containing a blister pack of 8 orally disintegrating tablets. Each ODT contains 75 mg rimegepant.

This example contemplates that the administration of a combination of dual-route aspirin and oral ketamine would provide similar analgesic efficacy to Nurtec with respect to analgesic efficacy at 60 min and 120 minutes in ED patients with acute headache.

Subjects: Patients 18 years of age and older presenting to the ED with acute headache (defined as HA lasting no more than 1 week) and an initial pain score of 5 or more on a standard 11-point (0 to 10) numeric rating scale and requiring oral analgesia as determined by the treating attending physician. Patients' screening and enrollment will be performed by study investigators and research assistants. All patients will be enrolled at various times of the day when study investigators will be available for patient enrollment and an ED pharmacist will be available for medication preparation.

Eligibility Criteria: Patients 18 years of age and older presenting to the ED with acute headache (<7 days) and an initial pain score of 5 on a standard 11-point (0 to 10) numeric rating scale. Patients will have to be awake, alert, and oriented to person, place, and time, and will be able to demonstrate understanding of the informed consent process and content. Patients also will have to demonstrate ability to verbalize the nature of any adverse effects they might experience as well as to express their pain severity by using the NRS.

Exclusion Criteria: Patients with altered mental status, allergy to aspirin/ketamine/rimegepant, pregnant patients, unstable vital signs (systolic blood pressure <90 or >180 mm Hg, pulse rate <50 or >150 beats/min, and respiration rate <10 or >30 breaths/min), inability to provide consent, consumption of Aspirin/NSAID's within 6 hours of arrival to the ED, or acetaminophen within 4 hours of arrival to the ED, active PUD, history of GI Hemorrhage, history of renal and hepatic insufficiency, past medical history of alcohol or drug abuse, or schizophrenia, as well as clinical findings concerning for acute intracranial process, acute infections process, or vascular catastrophe, pregnant patients and breastfeeding patients.

Design: This is a prospective, open-label, equivalence trial evaluating and comparing analgesic efficacy and safety of a combination of dual-route aspirin and oral ketamine, and Nurtec in adult patients presenting to the ED of Maimonides Medical Center with acute headache. Upon meeting the eligibility criteria, patients will be offered to participate in the study.

Data Collection Procedures: Each patient will be approached by a study investigator for acquisition of written informed consent and Health Insurance Portability and Accountability Act authorization after being evaluated by the treating emergency physician and determined to meet study eligibility criteria. When English will not be the participant's primary language, a language-appropriate consent form will be used and non-investigator, hospital-employed, trained interpreters or licensed telephone interpreter will assist in acquisition of informed consent. Baseline pain score will be determined with an 11-point numeric rating scale (0 to 10), described to the patient as "no pain" being 0 and "the worst pain imaginable" being 10. A study investigator will record the patient's body weight and baseline vital signs. All data will be recorded on data collection sheets, including patients' sex, demographics, medical history, and vital signs, and entered into SPSS (version 24.0; IBM Corp) by the research manager. Confirmation of written consent acquisition for all participants, and statistical analyses will be conducted by the statistician (Michael Silver), who will work independently of any data collection.

Study Set-up. The on-duty ED pharmacist will prepare medications in the following fashion: the combination of dual-route aspirin (325 mg) and oral ketamine (0.85 or 1 mg/kg) (Combo) and Nurtec that are provided by the sponsor will be placed in the medication cups according to a randomization list generated by the research manager by SPSS (version 24.0; IBM Corp, Armonk, N.Y.). The oral dose of ketamine will be prepared by using an injectable form of ketamine at 0.85 or 1 mg/kg dose and matching (by volume) placebo (normal saline). This weight-based dose of ketamine and saline placebo will be placed in the syringe and sweetener will be added to offset the bitter taste of ketamine. The Combo group will receive the combination medication cup and oral ketamine syringe, and Nurtec group will receive Nurtec ODT blister containing 75 mg of rimegepant in the medication cup and oral placebo syringe.

The research associate will deliver both syringes and medication cups to the patients' nurse who will administer medication. Study investigators will record pain scores and adverse effects at 30, 60, 90, and 120 minutes. If patients reported a pain numeric rating scale score of 5 or greater and requested additional pain relief, the rescue analgesic (s) and routes will be chosen upon treating attending's discretion. Patients will be closely monitored for adverse effects during the entire study period (up to 120 minutes) by study investigators. Common adverse effects that are associated with oral ketamine are felling of unreality, dizziness, nausea, vomiting, and sedation. Common adverse effects that are associated with Combo are nausea, dyspepsia, epigastric discomfort. Common adverse effect that is associated with Nurtec include nausea.

Data Analysis: Data analyses will include frequency distributions and independent-sample t-test to assess differences in pain scores at the various intervals. Mixed-model linear regression will be used to compare changes in pain numeric rating scale across time points. For categorical outcomes (e.g., complete resolution of pain), a $X^2$ or Fisher's exact test will be used to compare outcomes at 60 and 120 minutes. Based on the validation of a verbally administered rating scale of acute pain in the ED and the comparison of verbal and visual pain scales, we will use a primary outcome consisting of a minimal clinically meaningful difference of 2 points between two groups at the 60-minute and 120-minute pain assessment.

Contemplated Outcomes: The primary outcome will include a comparative reduction of pain scores on numeric rating pain scale (NRS) at 60 minutes from the baseline. The secondary outcomes will include a need for rescue analgesia, rates of adverse effects, and change in pain score up to 120 minutes.

SAE Reporting: Any serious adverse event, requiring intervention, will be reported to the IRB within 24 hours of discovery by the research staff. Less serious adverse events will be reported within a week of discovery. There are known expected outcomes and side effects to the procedures and medications being received and these are the same risks/side effects as the standard of care—these will be reported if they are serious and require intervention.

Example 4. Oral VTS-K (Combination of VTS-Aspirin and Oral Ketamine) as an Adjunct to Oral Antidepressant Therapy in Treatment of Major Depressive Disorder This example tests the use of ketamine in treating depression. It is contemplated that 486 mg of aspirin (dual-route intraoral/oral administration) and 1.2 mg/kg ketamine (dual-route intraoral/oral administration) as an adjunct to oral antidepressant treatment will result in reduction of depressive symptoms based on the change in score from baseline to day 7 after initial dose on the Montgomery-Åsberg Depression Rating Scale (MADRS).

Subjects: This is a prospective observational proof of concept study of medically stable (based on the physical examination, history, and vital signs) adults patients 18 years of age and older with a diagnosis of major depressive disorder without psychotic features according to DSM-IV-TR criteria presenting to the psychiatric clinic for evaluation. Patients to have a score ≥22 on the Montgomery-Åsberg Depression Rating Scale (MADRS) on day 1 before dosing. Participants ought to agree to continue oral antidepressant therapy they were receiving prior to the enrollment into the study.

Eligibility Criteria:

Adult patients with TRD with MADRS score >22 upon presentation to the clinic.

Participants ought to agree to standard-of-care treatment with one or more non-investigational antidepressants.

Participants ought to agree to continue oral antidepressant therapy they were receiving prior to the enrollment into the study. All participants must agree to provide and informed consent.

Exclusion Criteria:

Adult patients with recent or current suicidal ideation with an intent to act, homicidal ideations with an intent to act, intellectual disability, major depressive disorder with psychosis, posttraumatic stress disorder, obsessive-compulsive disorder, substance use disorder, antisocial personality disorder, borderline personality disorder, or a current or past diagnosis of a psychotic disorder altered mental status, allergy to aspirin and ketamine, pregnant patients, unstable vital signs (systolic blood pressure <90 or >180 mm Hg, pulse rate <50 or >150 beats/min, and respiration rate <10 or >30 breaths/min), consumption of Aspirin or NSAID's within 6 hours of arrival to the ED, active PUD, history of GI Hemorrhage, and history of renal and hepatic insufficiency.

Design:

This is a prospective observational proof of concept study of adult patients 18 years of age and older with a diagnosis of TRD without psychotic features according to DSM-IV-TR criteria presenting to the psychiatric clinic for evaluation. Eligible participants will receive 486 mg of aspirin (dual-route intraoral/oral administration) and 1.2 mg/kg ketamine (dual-route intraoral/oral administration) as an adjunct to oral antidepressant treatment twice a week for 1 week (on day 1 and 4 for the week). All participants will be observed for 4 hours in the outpatient setting after receiving the medication and their depressive symptoms will be assessed at 4-hour mark by MADRS Scale and QIDS-SR scale (Quick Inventory of Depressive Symptomatology-Self Report) and their adverse effect related to VTS=K administration will be assessed by using the Clinician Administered Dissociative State Scale (CADSS) and MOAA/S scale and RASS scale.

Study Set Up

The on-duty pharmacist will prepare an oral dose of ketamine by using an injectable form for parenteral use. The on-duty ED pharmacist will prepare a syringe/medication cup containing the medication according to the predetermined list, which will be created in SPSS (version 24; IBM Corp, Armonk, N.Y.). The oral sweetener solution of 1 ml will be added to the syringe containing ketamine. The research pharmacist will deliver syringes/medication cup to the patients' nurse who will administer medication. Subjects will be instructed to first suck off the outer layer of aspirin for about 30-60 seconds and then swallow the tablet. The oral antidepressant medication will be initiated or optimized for all participants on day 1. Participants taking a recently initiated antidepressant at screening could continue the antidepressant at the same dosage during treatment with study drug. Study investigators will record VS, and adverse effects at 30 minute, 60 minutes, 2 hours, and 4 hours. Patients will be closely monitored for adverse effects during the entire observation period (for up to 2-4 hours) by study investigators.

Efficacy Assessments

Research associates and study investigators will assess depressive symptom severity with the Montgomery-Åsberg Depression Rating Scale (MADRS) on day one and on day 4 and day 7 (for days 1 and 4 this will include pre-dose, 40 minutes, 120 minutes, and 240 minutes post-dose). Patients will also be screened using the Beck Scale for Suicide Ideation and their sense of hopelessness using the Beck Hopelessness Scale before dosing and 4 hours after dosing on day one and pre-dosing on days 4, and 7.

Safety Assessments

Vital signs will be checked before medication administration and 1, 2, 4 hours post-drug administration during the study period. Adverse events will be monitored throughout the study. The Clinician-Administered Dissociative States Scale (CADSS) will be administered before dosing and at 40 minutes, 2 hours, and 4 hours after dosing on day 1 and day 4. In addition, a Modified Observer's Alertness/Sedation Scale (MOAA/S) will be used to assess the level of sedation.

Common adverse effects that are associated with oral ketamine are felling of unreality, dizziness, nausea, vomiting, sedation, and dissociation. Common adverse effects are associated with VTS-Aspirin are nausea, dyspepsia, epigastric discomfort, Data Collection Procedures: Each patient will be approached by a study investigator for acquisition of written informed consent and Health Insurance Portability and Accountability Act authorization after being evaluated by the treating psychiatry physician and determined to meet study eligibility criteria. When English will not be the participant's primary language, a language-appropriate consent form will be used and non-investigator, hospital-employed, trained interpreters or licensed telephone interpreter will assist in acquisition of informed consent. Baseline Depression score via MADRS will be recorded by a study investigator. All data will be recorded on data collection sheets, including patients' sex, demographics, medical history, and vital signs, and entered into SPSS (version 24.0; IBM Corp) by the research manager. Confirmation of written consent acquisition for all participants, and statistical analyses will be conducted by the statistician who will work independently of any data collection.

Data Analysis: Data analyses will include mixed-effect model with repeated measures with baseline MADRS score as covariate; time by treatment interaction as fixed effect and patient as random effect.

Expected Outcomes:

The primary outcome will include a change in depressive symptoms on the Montgomery-Åsberg Depression Rating Scale (MADRS) from the baseline (pre-dose day 1) and day 7.

The secondary outcomes will include: a change in depressive symptoms on the Montgomery-Åsberg Depression Rating Scale (MADRS) from the baseline (pre-dose on day 1 and 4) and 4 hours post-medication administration.

Rates of Side effects will be reported by using the Clinician-Administered Dissociative States Scale (CADSS), Side Effect Rating Scale for Dissociative Anesthetics (SERSDA), and Modified Observer's Alertness/Sedation Scale (MOAA/S). The SERSDA scale includes fatigue, dizziness, nausea, headache, feeling of unreality, changes in hearing, mood change, general discomfort, and hallucinations with severity of each graded by patients on a five-point scale, with "0" representing the absence of any adverse effects and "4" representing a severely bothersome side effect.

SAE Reporting: Any serious adverse event, requiring intervention, will be reported to the IRB within 24 hours of discovery by the research staff. Less serious adverse events will be reported within a week of discovery. There are known expected outcomes and side effects to the procedures and medications being received and these are the same risks/side effects as the standard of care—these will be reported if they are serious and require intervention.

Example 5. Therapeutic Effects of Dual Ketamine/Aspirin

This example presents the results from a trial as outlined in Example 1, in comparison with data collected from similar trials with other agents and the same testing protocol and pain measurement scales, in the same medical center by the same research team and same statistical methods. The testing agents and dosages are listed in Table 1.

TABLE 1

Agents and Doses

| No. | Agent | Dose |
| --- | --- | --- |
| 1 | Morphine (IV) | 0.1 mg/kg |
| 2 | Morphine Sulfate Immediate Release (MSIR) (oral) | 15 mg |
| 3 | Percocet (oral) | 10 mg |
| 4 | Dual route ketamine + aspirin (intraoral + oral) | 0.5 mg/kg ketamine |
| 5 | Ketamine (IV) | 0.3 mg/kg |
| 6 | Nebulized ketamine | Mixed dose |
| 7 | Ibuprofen (oral) | Mixed dose |
| 8 | Ketorolac (IV) | |

The efficacy to reduce acute musculoskeletal pain by each agent was measured as described in Example 1. The results are presented in FIG. 1. As expected, IV morphine had the highest efficacy, resulting in a 5.1-point reduction of acute musculoskeletal pain. The least efficacious was oral ibuprofen (2 points). IV ketamine and intranasal (nebulized) ketamine were both effective, achieving a reduction of about 4 points, similar to oral morphine and Percocet.

Quite unexpectedly, the dual-route ketamine and dual-route aspirin achieved a 3.84-point reduction of acute musculoskeletal pain. As explained above, it has been demonstrated that the oral bioavailability of ketamine is about ⅕ of the availability via IV injection. Here, the measured efficacy of dual-route ketamine (0.5 mg/kg) and aspirin (3.84 points) is equivalent to that of IV ketamine (0.3 mg/kg) (3.8 points). Therefore, these data suggest that the dual-route ketamine (with aspirin) at 0.5 mg/kg is equivalent to conventional oral ketamine at 1.5 mg/kg. This is a three-fold increase of efficacy as compared to the conventional oral ketamine.

A typical side effect of ketamine is sedation, which was measured with a Richmond Agitation-Sedation Scale (RASS) as described in Table 2A. The results are compared to published ones that either used the RASS scale or a MOAA/S scale (Modified Observer's Assessment of Alertness/Sedation) which is described in Table 2B. The published data include those from Motov 2017 (Motov S. et al., *Ann Emerg Med.* 2017 August; 70(2):177-184), Motov 2019 (Motov S. et al., Am J Emerg Med, 2019 February; 37(2): 220-227), and the drug label of Spravato® esketamine (intranasal ketamine).

TABLE 2A

Sedation Measurement Scores - RASS

| Score | Description |
| --- | --- |
| +4 | Combative |
| +3 | Very agitated |
| +2 | Agitated |
| +1 | Restless |
| 0 | Alert and calm |
| −1 | Drowsy |
| −2 | Light sedation |
| −3 | Moderate sedation |
| −4 | Deep sedation |
| −5 | Unarousable sedation |

TABLE 2B

Sedation Measurement Scores - MOAA/S

| Score | Description |
| --- | --- |
| 5 | Responds readily to name spoken in normal tone |
| 4 | Lethargic response to name spoken in normal tone |
| 3 | Responds only after name is called loudly and/or repeatedly |
| 2 | Responds only after mild prodding or shaking |
| 1 | Responds only after painful trapezius squeeze |
| 0 | No response after painful trapezius squeeze |

The results are shown in FIG. 2, along with control data from the publications. Only 8% patients who received the dual-route ketamine and aspirin had any sedation side effect, and only 4% reported moderate or above sedation side effects (RASS <=−3 or MOAA/S<=3). Such rates are considerably lower than both IV ketamine and intranasal ketamine. Given that the dual-route ketamine and aspirin was as efficacious as IV and intranasal ketamine, its greatly reduced sedation side effect was truly a surprise.

Another common side effect of ketamine is dissociation, which was measured with a Side Effects Rating Scale of Dissociative Anesthetics (SERSDA) scale as described in Table 3A. The results are compared to published ones that either used the SERSDA scale or a Clinician-Administrated Dissociative States Scale (CADSS) which is described in Table 3B. The published data include those from Motov 2017, Motov 2019, and the drug label of Spravato® esketamine (intranasal ketamine).

TABLE 3A

Dissociation Measurement Scale - SERSDA

| Score | Description |
| --- | --- |
| 0 | No change |
| 1 | Weak |
| 2 | Modest |
| 3 | Bothersome |
| 4 | Very Bothersome |

TABLE 2B

Dissociation Measurement Scale - CADSS 27 questions
0-4 points each
>4 increase "positive"

The results are shown in FIG. 3, along with control data from the publications. Only 4% patients who received the dual-route ketamine and aspirin had any dissociation side effect (SERSDA Unreality; *CADSS >4 pt incurrence), and none (0%) reported significant dissociation side effects (SERSDA Unreality: Bothersome+; *CADSS >10 pt incurrence). Such rates are considerably lower than both IV ketamine and intranasal ketamine. Given that the dual-route ketamine and aspirin was as efficacious as IV and intranasal ketamine, its greatly reduced dissociation side effect was again truly a surprise.

Example 6

This example provides the results of additional clinical testing of various compositions of the instant disclosure, in terms of their pain reduction efficacy and associated adverse effects.

This new study was an extension of the study in Example 5, at the same site, also with patients with acute musculoskeletal pain in the ER (e.g., acute back pain, or a wrist fracture). The tested formulations are described below.

In a first analysis, data collected from only patients having fractures were analyzed. They were divided into an aspirin/ketamine (Any ASA/KET) group (N=11) and a dual-route (intraoral and oral) ketamine (Dual Route KET) group (N=4). Primarily, the safety endpoint was examined defined as any SERSDA scores of 3 or higher (i.e., moderately or severely "bothersome"). As shown in FIG. 4, none of the patients that received both aspirin and ketamine (Any ASA/KET) had any moderate or severe adverse events, while 25% of the patients receiving dual-route ketamine (Dual Route KET) had adverse events.

Figure 5:
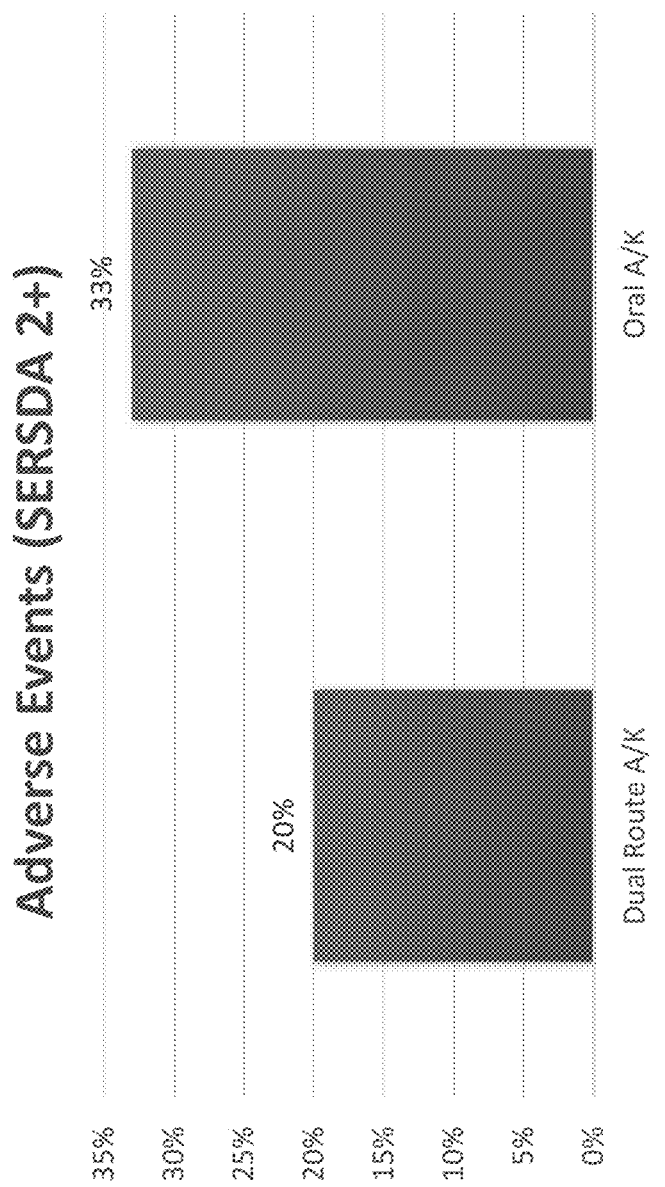
FIG. 5 compares the SERSDA2+ adverse events experienced in patients of different groups.

The aspirin/ketamine group was further divided, into a dual route aspirin+dual route ketamine (Dual Route A/K) arm and an oral aspirin+oral ketamine (Oral A/K) arm. In this comparison, all adverse events of SERSDA2+ were examined. As shown in FIG. 5, the Oral A/T arm had significantly higher (65% more) SERSDA2+ events than the Dual Route A/K arm.

Figure 6:
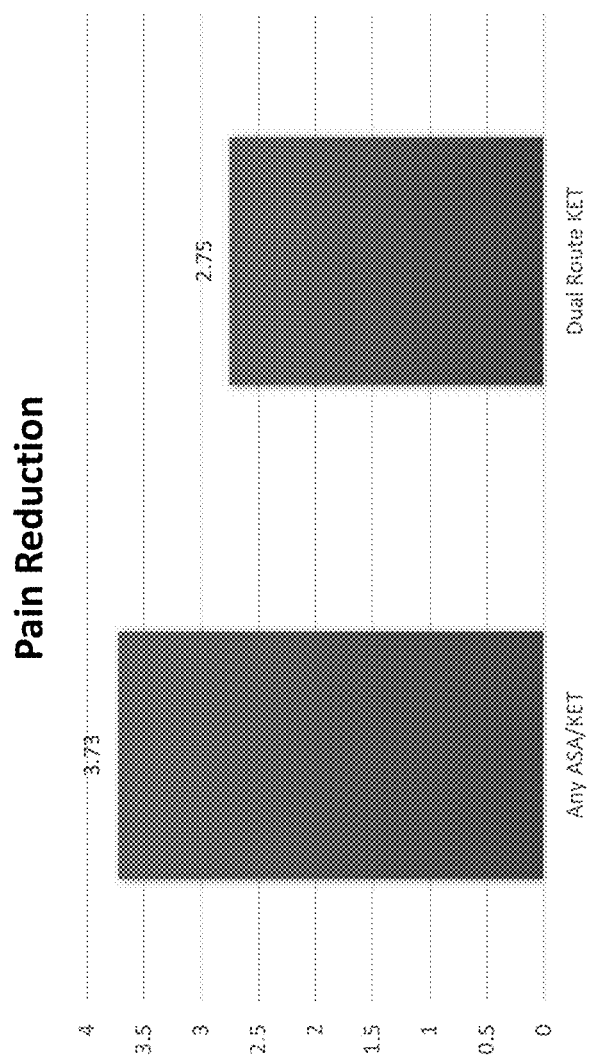
FIG. 6 compares the pain reduction in patients of different groups.
Figure 7:
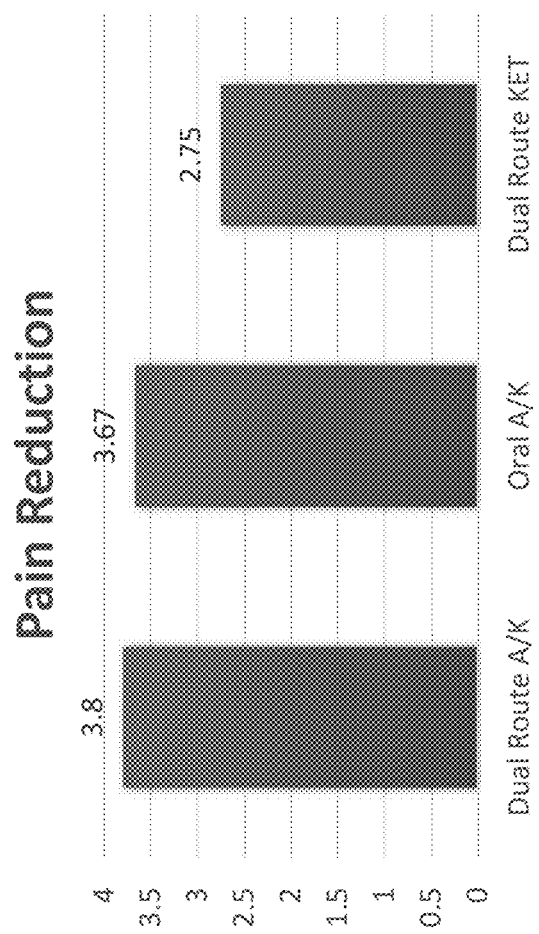
FIG. 7 compares the pain reduction in patients of different groups.

In the second analysis, also only with patients having fractures, patients with any combination of ASA/KET (Any ASA/KET) were compared to patients that received dual-route (intraoral and oral) ketamine (Dual Route KET). As shown in FIG. 6, the pain reduction efficacy of the ASA/KET combination was about 36% higher than the Dual Route KET arm. When the ASA/KET group was divided into two subgroups (i.e., Dual Route A/K and oral aspirin+oral ketamine (Oral A/K)), both subgroups outperformed dual-route ketamine (FIG. 7).

Figure 8:
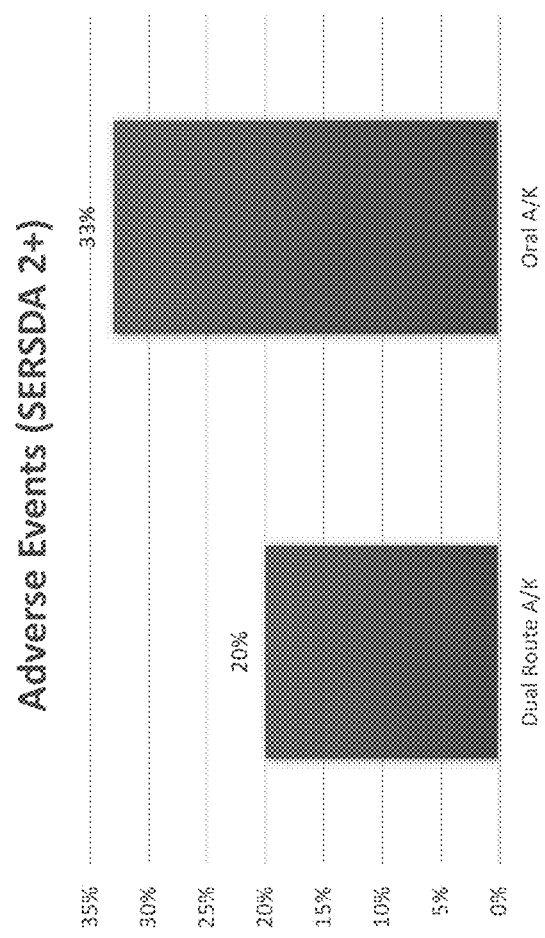
FIG. 8 compares the SERSDA2+ adverse events experienced in patients of different groups.

In the third analysis, patients that received oral aspirin and oral ketamine (Oral A/K, N=25) were compared to those who received Dual Route A/K (N=10). None of the patients experienced SERSDA3+. The comparison of SERSDA2+ events is shown in FIG. 8, which shows that 65% more ASA/KET patients had adverse events than Dual Route A/K patients.

Figure 9:
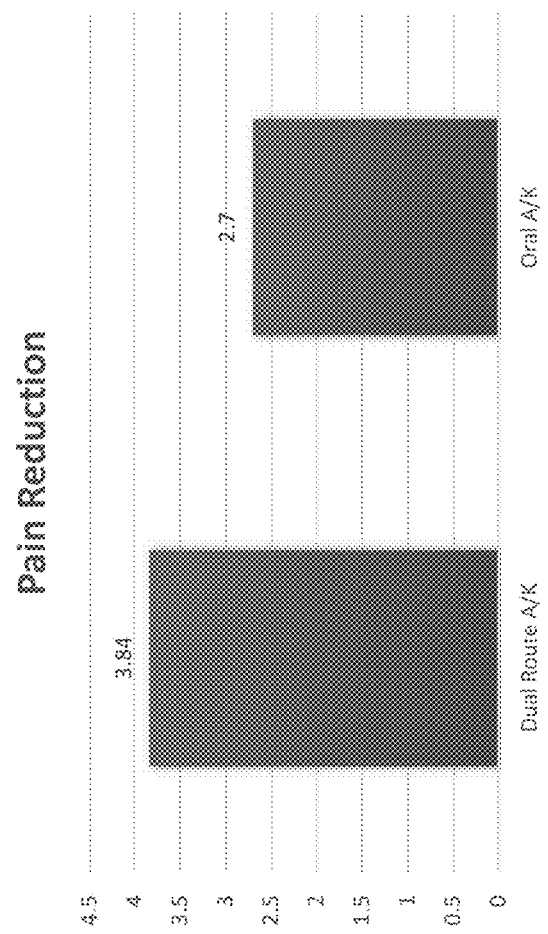
FIG. 9 compares the pain reduction in patients of different groups.
Figure 10:
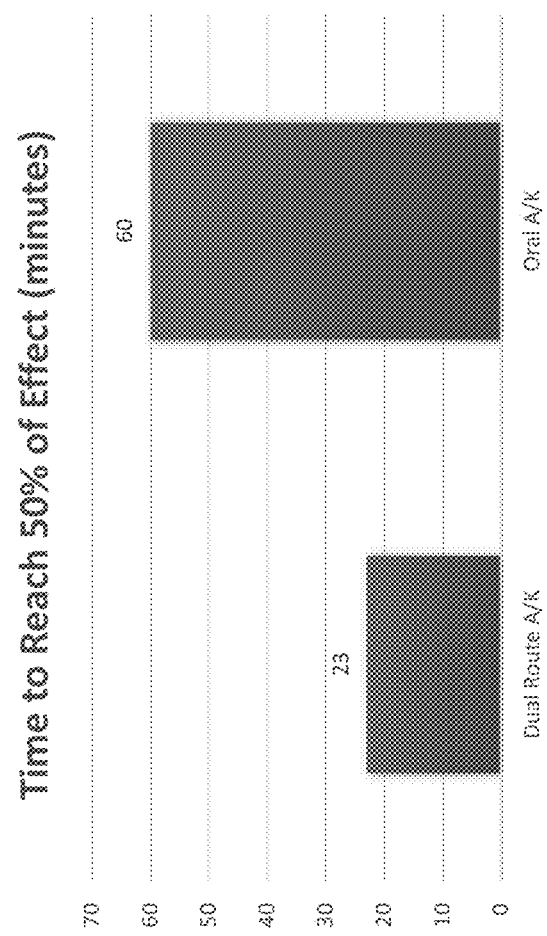
FIG. 10 compares time to reach 50% pain reduction in patients of different groups.

In terms of pain reduction, Dual Route A/K patients had 42% more pain reduction, 3.84 vs. 2.7, as shown in FIG. 9. Also, in terms of time to onset (50% of pain reduction), the Dual Route A/K arm experienced much quicker pain relief, 23 minutes vs. 60 minutes, as shown FIG. 10.

It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

The invention claimed is:

1. A method for administering ketamine to a subject or treating pain in the subject, comprising administering to the subject (a) a first composition comprising a first amount of ketamine and (b) a second composition comprising a second amount of ketamine, wherein the first composition disintegrates or dissolves intraorally providing rapid release of the ketamine of the first composition, and the second composition is ingested and released in the gastrointestinal track of the subject, and wherein the second composition is enclosed within the first composition in the form of a bilayer tablet.

2. The method of claim 1, wherein the first composition comprises at least about 20% of the therapeutically effective amount of ketamine and the second composition comprises at least about 20% of the therapeutically effective amount of ketamine.

3. The method of claim 1, wherein the first composition is chewable.

4. The method of claim 3, wherein the second composition is compressed.

5. The method of claim 4, wherein the second composition comprises enteric coating.

6. The method of claim 1, wherein the pain is acute musculoskeletal pain.

* * * * *